United States Patent [19]

Teng et al.

[11] Patent Number: *5,070,087
[45] Date of Patent: Dec. 3, 1991

[54] ARYL(ALKYL AND ALKYLENE)-N-((PHENOXY AND PHENYLTHIO)ALKYL) AMINOHETEROCYCLICS AS CARDIOVASCULAR, ANTIHISTAMINIC, ANTISECRETORY AND ANTIALLERGY AGENTS

[75] Inventors: Lina C. Teng; David A. Walsh; James R. Shanklin, Jr., all of Richmond, Va.

[73] Assignee: A. H. Robins Company, Incorporated, Richmond, Va.

[*] Notice: The term of this patent subsequent to Mar. 7, 2006, has been disclaimed.

[21] Appl. No.: 349,247

[22] Filed: May 8, 1989

[51] Int. Cl.$^5$ .................. A61K 31/445; A61K 31/40; A61K 31/55
[52] U.S. Cl. .................................. 514/212; 514/317; 514/318; 514/426; 514/424; 514/428
[58] Field of Search ............... 514/317, 318, 424, 426, 514/212, 428

[56] References Cited

U.S. PATENT DOCUMENTS

| | | | |
|---|---|---|---|
| 3,759,928 | 9/1973 | Zivkovik | 546/192 |
| 3,806,526 | 4/1974 | Carr et al. | 546/237 |
| 3,965,257 | 6/1976 | Carr et al. | 514/317 |
| 3,984,559 | 10/1976 | Weinstock | 514/343 |
| 4,035,372 | 7/1977 | Deason et al. | 546/234 |
| 4,163,790 | 8/1979 | Franko et al. | 514/235 |
| 4,810,713 | 3/1989 | Yanni et al. | 514/317 |

Primary Examiner—Mukund J. Shah
Assistant Examiner—E. C. Ward
Attorney, Agent, or Firm—Richard K. Jackson

[57] ABSTRACT

A method of treating cardiac dysfunction, the effects of histamine, and gastric secretion excesses with aryl(alkyl and alkylene)-N-[(phenoxy and phenythio)alkyl-]aminoheterocyclics corresponding to the formula:

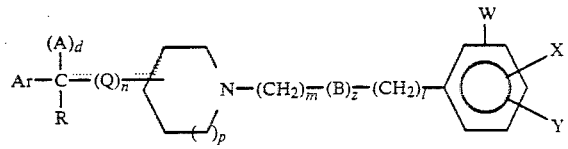

wherein Ar is phenyl or substituted phenyl; R is phenyl, substituted phenyl, pyridinyl or cycloalkyl; A is hydrogen, hydroxy, cyano, amido and amino; Q is —CH$_2$—, —CH—, or —CHOH—; d and n are zero or one and the dotted lines form double bonds consistent with the valence of carbon; p is zero, one or two; m is one to six inclusive; B is oxygen, nitrogen, sulfur, sulfinyl or sulfonyl; z is zero or one; l is zero or one; W is hydrogen, loweralkyl, halo, nitro, loweralkoxy or hydroxy; X is hydrogen, loweralkyl, halogen, loweralkoxy or hydroxy; Y is —CH(OH)CH$_2$OH, —CH(OH)C(O)OH, —C(O)C(O)OH, —C(O)CH$_2$OH, —C(O)C(O)OCH$_3$, —C(O)C(O)OC$_2$H$_5$, —CH$_2$C(O)OC$_2$H$_5$, —CH(OH)C(O)OCH$_3$, —CH(OH)C(O)OC$_2$H$_5$ or —C(O)CH$_2$OC(O)CH$_3$; and the pharmaceutically acceptable salts thereof; in addition to the above methods of treatment, compounds wherein (B)$_z$ is oxygen are useful in a method of treating Gell and Coombs type 1 allergic responses in mammals.

5 Claims, No Drawings

ARYL(ALKYL AND ALKYLENE)-N-((PHENOXY AND PHENYLTHIO)ALKYL) AMINOHETEROCYCLICS AS CARDIOVASCULAR, ANTHIHISTAMINIC, ANTISECRETORY AND ANTIALLERGY AGENTS

BACKGROUND OF THE INVENTION

1. Field of Invention

The present invention relates to certain aryl(alkyl and alkylene)-N-[(phenoxy and phenylthio)alkyl]pyrrolidines, piperidines, tetrahydropyridines and homopiperidines useful in novel methods of treating cardiovascular dysfunctions, countering effects of histamine in allergies, countering gastric secretion excesses, and inhibiting Type I allergic responses (Gell and Coombs Classification of Immune Responses) in a living mammal body.

2. Information Disclosure Statement

U.S. Pat. No. 3,956,296 and a divisional patent thereof, U.S. Pat. No. 4,032,642 disclose certain compounds among which some would fall within a generic structure as follows:

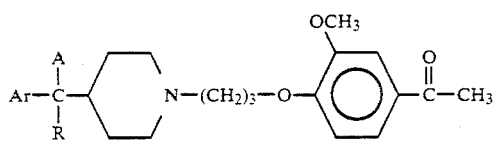

wherein Ar is 4-fluorophenyl or phenyl; R is cyclohexyl; 3-trifluoromethylphenyl, 4-fluorophenyl or phenyl; and A is hydrogen or hydroxy. Certain compounds of the present invention have been found to be metabolites of this group of compounds as explained hereinbelow.

U.S. Pat. No. 3,922,276 discloses compounds among which some would fall within a generic structure as follows:

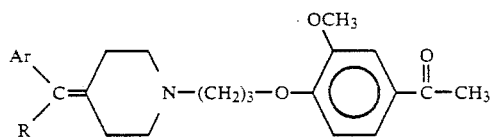

wherein Ar is 4-fluorophenyl or phenyl; and R is cyclohexyl, 4-fluorophenyl, 3-trifluoromethylphenyl, or phenyl. Certain of the compounds of the present invention have been found to be metabolites of this group of compounds as explained hereinbelow.

A copending U.S. patent application Ser. No. 819,701 filed on 1-17-86 by J. R. Shanklin, Jr., et al., and South African Patent No. 86/4522 issued on 2/25/87 disclose compounds among which some would fall within the formula:

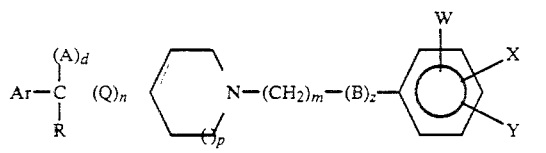

wherein Ar, R, A, d, n, p, m, B, z, and X are approximately as defined hereinbelow under Formula I, and wherein Y is never as defined hereinbelow under Formula I. It should be understood that the compounds useful in the present invention always have a terminal phenyl group substituted by a Y radical which is distinct from compounds disclosed in prior art. Certain of the compounds of the present invention have been found to be metabolites of certain compounds disclosed in the Shanklin application.

U.S. Pat. No. 4,810,713, issued on 3/7/89 by J. M. Yanni, et al., and South African Patent No. 86/4458 issued on 2/25/87, disclose certain compounds among which some would fall within the generic structure which follows:

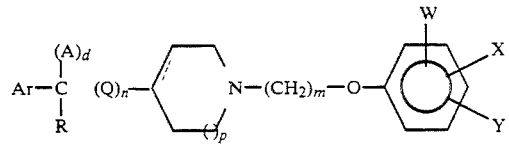

wherein Ar, R, n, p, m, W and X are approximately as defined hereinbelow under Formula I; A is hydroxy or hydrogen; and Y is never as defined hereinbelow under Formula I. It should be understood that these compounds are a special subclass of the compounds disclosed in the earlier cited U.S. patent application Ser. No. 819,701 of Shanklin, et al.

U.S. Pat. No. 3,806,526 discloses 1-aroylalkyl-4-diphenylmethylpiperidines having antihistaminic, antiallergenic and bronchodilator activity. In contrast, the compounds useful in the present invention have an aryloxyalkyl radical on piperidine and pyrrolidine nitrogen rather than an aroylalkyl radical.

U.S. Pat. No. 4,163,790 discloses compounds which fall within a generic structure as follows:

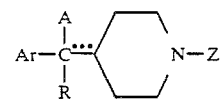

wherein Ar and R are phenyl and p-fluorophenyl and Z is hydrogen, acetyl, p-fluorobenzoylpropyl, carbamoyl, N-methylcarbamoyl, N,N-dimethylcarbamoyl, phenylcarbamoyl, or N-(ω-morpholinoethyl)carbamoyl; A is hydrogen, hydroxy or forms a double bond as indicated by the dotted line. The compounds were active in increasing coronary blood flow; however, the compounds while substituted in the 4-piperidine position and also disclosed in the other above-mentioned patents, differ substantially in structure from the compounds of the present invention in the substitution in the 1-position of the piperidine radical and are not within the scope of generic formulas hereof of compounds for novel treatment methods.

1-Benzyl-(α,α-diphenyl)-4-methylenepiperidines of the formula

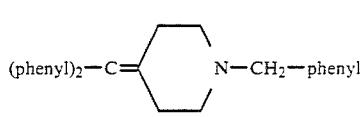

are disclosed in Ger. Offen. 2,800,919 as having anticonvulsant and vasodilating properties. Similar 1-benzyl-(α,α-diphenyl)-4-methylenepiperidines of the formula

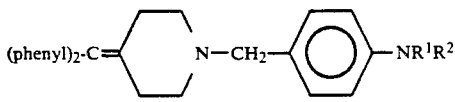

are disclosed in U.S. Pat. No. 4,035,372 as having vasodilating properties.

Piperidines of the general formula

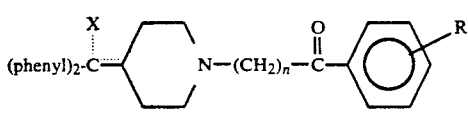

where X is H, OH, or forms a double bond to the piperidine ring are disclosed in U.S. Pat. No. 3,965,257 as having antihistamine activity.

4-(Diphenylmethylene)-1-benzylpiperidines of the general formula

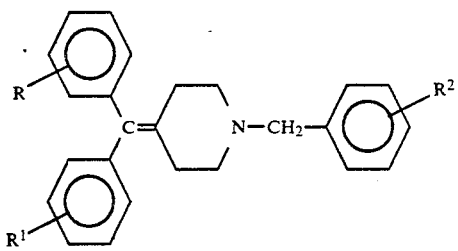

having hemodynamic, antiarrhythmic and antihistaminic activities are disclosed in U.S. Pat. No. 3,759,928.

U.S. Pat. No. 3,984,557 discloses compounds which fall within a generic structure as follows:

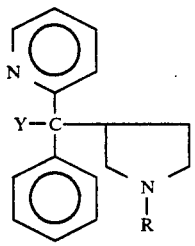

wherein R represents loweralkyl, lowercycloalkyl or phenyl-loweralkyl and Y is carbamoyl, cyano or hydrogen, the compounds having utility as antiarrhythmic agents. In the compounds of the present invention, the radical on the 1-position of the cycloalkylamino moiety has an aryloxy, arylamino or an aryl group other than phenyl on the alkyl chain.

SUMMARY OF THE INVENTION

The present invention is concerned with novel methods of correcting cardiovascular disturbances, countering the effect of histamine in allergies, countering gastric secretion excesses and inhibiting type I allergic responses in mammals using heterocyclic amines of the general Formulas I and Ia given hereinbelow. Compounds of Formula I are useful in controlling cardiac dysfunction, as antihistaminic agents and as antisecretory agents. Compounds of Formula I in addition to the above uses, are useful in controlling type I allergic responses in mammals (Gell and Coombs Classification of Immune Responses). Formula Ia is encompassed by Formula I.

Compounds of Formula I useful in the methods of treating cardiovascular dysfunction, as antihistaminic agents and as antisecretory agents in the present invention have the formula:

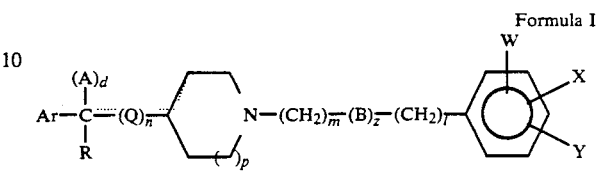

Formula I wherein
Ar is

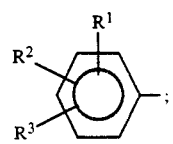

R is

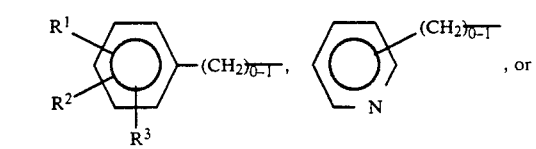

cycloalkyl-(CH$_2$)$_{\overline{0-1}}$;

A is hydrogen, hydroxy, cyano, C(O)NR$^4$R$^5$, or NR$^4$R$^5$;;

Q is —CH$_2$—, —CH— or $$-\underset{\underset{\text{OH}}{|}}{CH}-;$$

d and n are selected from zero or one and may be the same or different, and the dotted lines represent double bonds which may form consistent with the valence of carbon;

p is zero, one or two;

m is zero to six inclusive;

B is oxygen, nitrogen, thio, sulfinyl or sulfonyl; when z=1, m=2 to 6 z is zero or one;

l is zero or one;

W is hydrogen, loweralkyl, halo, nitro, loweralkoxy, or hydroxy;

X is hydrogen, loweralkyl, halo, loweralkoxy, or hydroxy;

Y is —CH(OH)—CH$_2$OH, —CH(OH)—C(O)OH, —C(O)—C(O)OH, —C(O)CH$_2$OH —C(O)C(O)OCH$_3$, —C(O)C(O)OC$_2$H$_5$, —CH$_2$C(O)OC$_2$H$_5$, —CH(OH)-C(O)OCH$_3$, —CH(OH)C(O)OC$_2$H$_5$, or —C(O)C-H$_2$OC(O)CH$_3$;

R$^1$, R$^2$ and R$^3$, same or different, are hydrogen, loweralkyl, halo, nitro, trifluoromethyl, cyano, loweralkoxy or hydroxy;

R$^4$ and R$^5$, same or different, are hydrogen, loweralkyl, phenyl, or phenylloweralkyl;

and the pharmaceutically acceptable salts thereof.

Compounds of Formula Ia useful in a method of controlling Gell and Coombs type I allergic responses in mammals have the formula:

Formula Ia

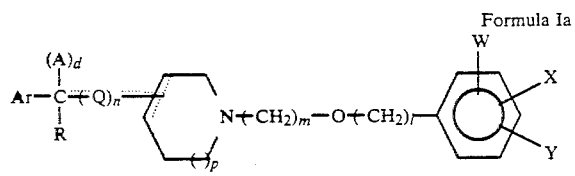

Ar is

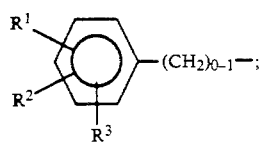

R is

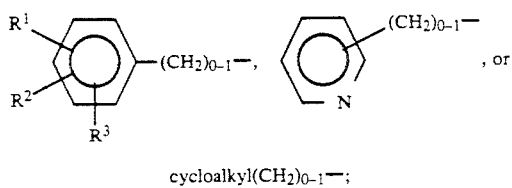

cycloalkyl(CH$_2$)$_{0-1}$—;

A is hydrogen, hydroxy, cyano, C(O)NR$^4$R$^5$, —NR$^4$R$^5$;

d is zero or one, and the dotted lines represent double bonds which may form consistent with the valence of carbon;

Q is —CH—, —CH$_2$— or

n is zero or one;
p is zero, one or two;
m is two to six inclusive;
l is zero or one;
W is hydrogen, loweralkyl, halo, nitro, loweralkoxy or hydroxy;
X is hydrogen, loweralkyl, halogen, loweralkoxy, or hydroxy;
Y is —CH(OH)—CH$_2$OH, —CH(OH)—C(O)OH, —C(O)—C(O)OH, —C(O)CH$_2$OH, —C(O)C(O)OCH$_3$, —C(O)C(O)OC$_2$H$_5$, .CH$_2$C(O)OC$_2$H$_5$, —CH(OH)-C(O)OCH$_3$, C(O)CH$_2$OC(O)CH$_3$, or CH(OH)-C(O)OC$_2$H$_5$;
R$^1$, R$^2$ and R$^3$, same or different, are hydrogen, loweralkyl, halo, nitro, trifluoromethyl, cyano, loweralkoxy or hydroxy;
R$^4$ and R$^5$, same or different, are hydrogen, loweralkyl, phenyl, or phenylloweralkyl;
and the pharmaceutically acceptable salts thereof.

Certain compounds have been included within the present application as examples even though their Y values are not defined under Inventors' Formulas I or Ia, and thus these compounds are not encompassed by the present invention. Their inclusion results from the discovery that they too, like certain compounds of the present invention, are metabolites of certain compounds disclosed in the above cited Shanklin, et al., U.S. patent application and the above cited Yanni, et al., U.S. patent. Through their inclusion as examples by the inventors of the present invention, a complete disclosure is made as to what metabolites were formed when certain compounds disclosed in the earlier cited Shanklin, et al., application, and Yanni, et al., U.S. patent were administered to mammals. The compounds in question, i.e., compounds wherein Y is the lowerhydroxyalkanyl radical or carboxy, are disclosed in U.S. patent application Ser. No. 154,390 of Shanklin, et al., filed on 2/10/88 to be useful in a method of treating cardiac dysfunction, countering gastric excess secretion, and countering the effects of histamine in allergies, the application is a continuation-in-part of the earlier cited Shanklin patent application. The compounds are also disclosed in U.S. patent application Ser. No. 159,940 of Yanni, et al., filed on 2/24/88 to be useful in a method of treating allergic responses associated with the Gell and Coombs Type 1 allergic reaction, the application is a continuation-in-part of the earlier cited Yanni, et al., application.

In the further definition of symbols in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula -O-loweralkyl.

The term "cycloalkyl" as used herein includes primarily cyclic alkyl radicals containing 3-7 carbon atoms inclusive and includes such groups as cyclopropyl, cyclobutyl, cyclopentyl, cyclohexyl, cycloheptyl and methylcyclohexyl and the like.

The term "halo" or "halogen" when referred to herein includes fluorine, chlorine, bromine, and iodine unless otherwise stated.

The term "central heterocyclic amine ring" refers to that portion of Formula I represented by

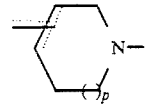

wherein the dotted line may represent a double bond. The term "saturated central heterocyclic amine ring" refers to the foregoing radical having no double bond.

The term "phenylloweralkyl" includes phenyl connected by hydrocarbon chains exemplified by loweralkyl above and wherein phenyl may be substituted by non-reactive or non-interfering radicals such as halo, loweralkyl, loweralkoxy and the like.

"Pharmaceutically acceptable salts" include acid addition salts, hydrates, alcoholates and quaternary salts of the compounds of Formula I which are physiologically compatible in warm-blooded animals. The acid addition salts may be formed by either strong or weak acids. Representative of strong acids are hydrochloric, hydrobromic, sulfuric and phosphoric acids. Representative of weak acids are fumaric, maleic, mandelic, tartaric, citric, oxalic, succinic, hexamic and the like. Suitable quaternary salts include the loweralkyl halides and loweralkyl sulfates.

The compounds of Formula I have been found to be calcium antagonists with potential use as coronary vasodilators, antihypertensives and antiarrhythmic agents and as such support the use of the term "useful in treating cardiac dysfunction."

The following charts I and II have been included to illustrate the preparation of Formula I and Formula Ia compounds from certain chemical precursors, and are not to be considered limiting to the invention contained herein, in as much as persons skilled in the art would understand how to prepare Formulas I and Ia compounds, and thus the charts therefore serve only as illustrations of several possible and available routes of preparation.

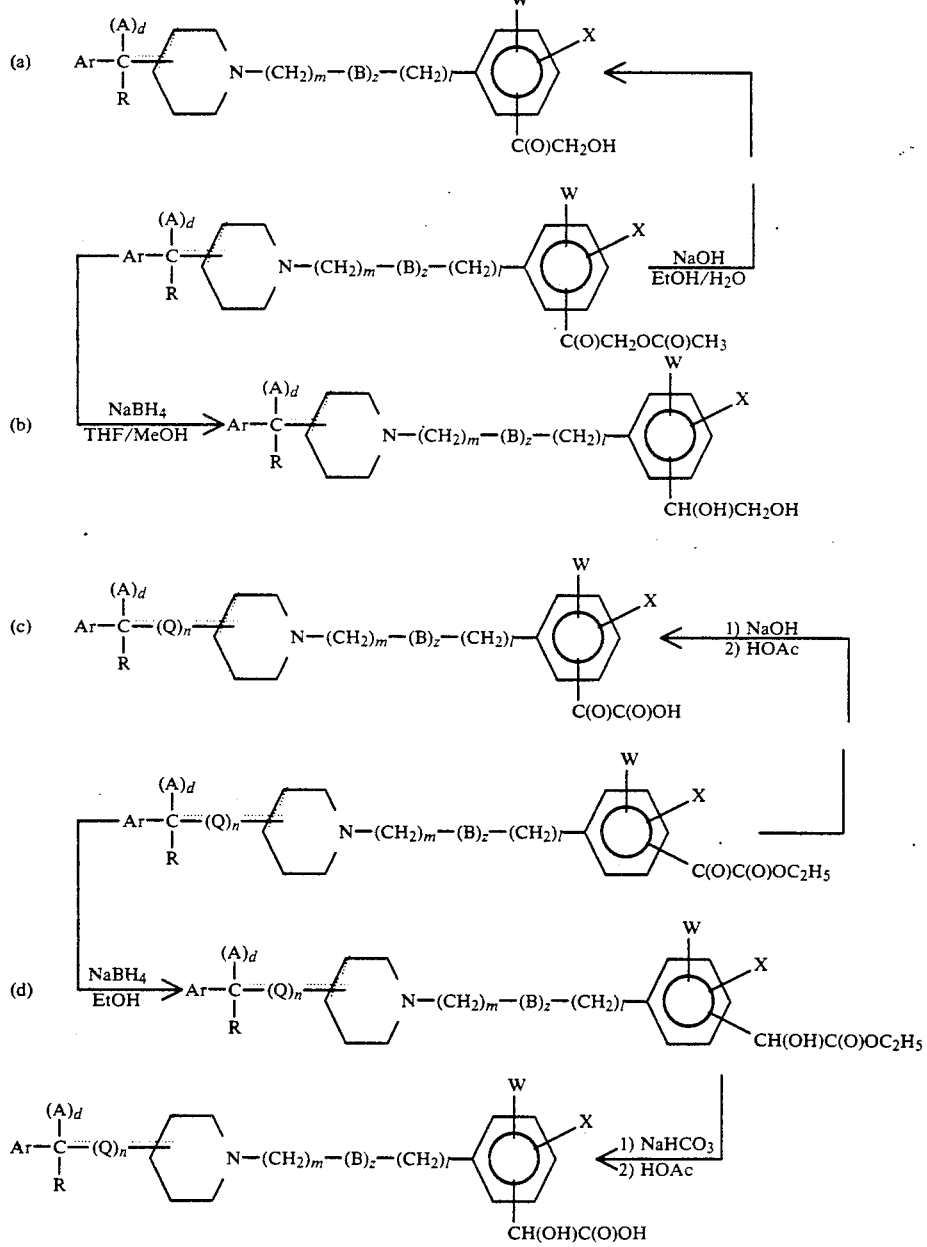

Chart II
Alternate Methods of Preparation for Compounds of Formula I
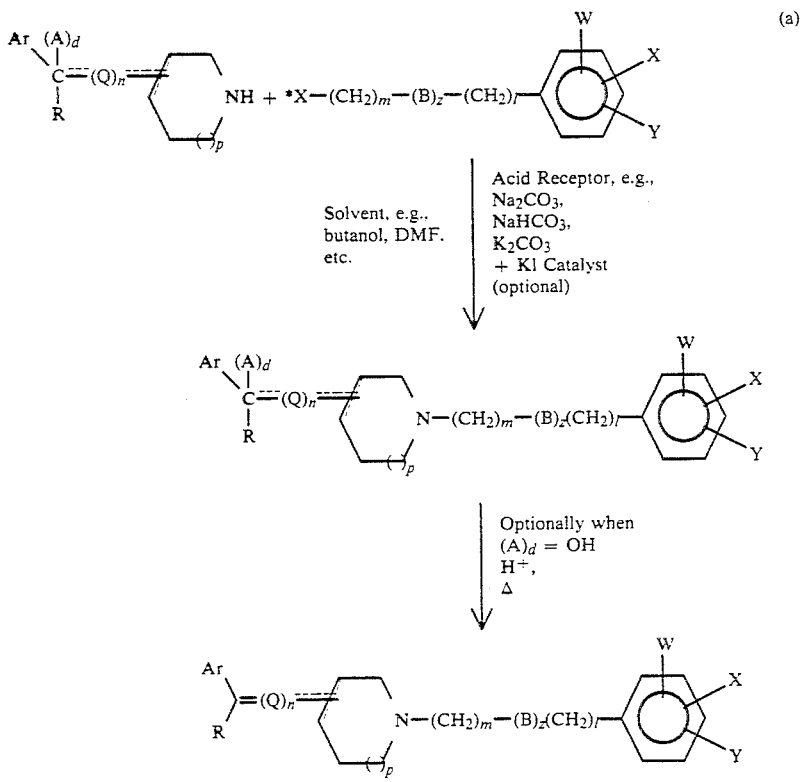
(a)
*X = halide
**d = 0
(R = Ar, n of (Q)n is zero)
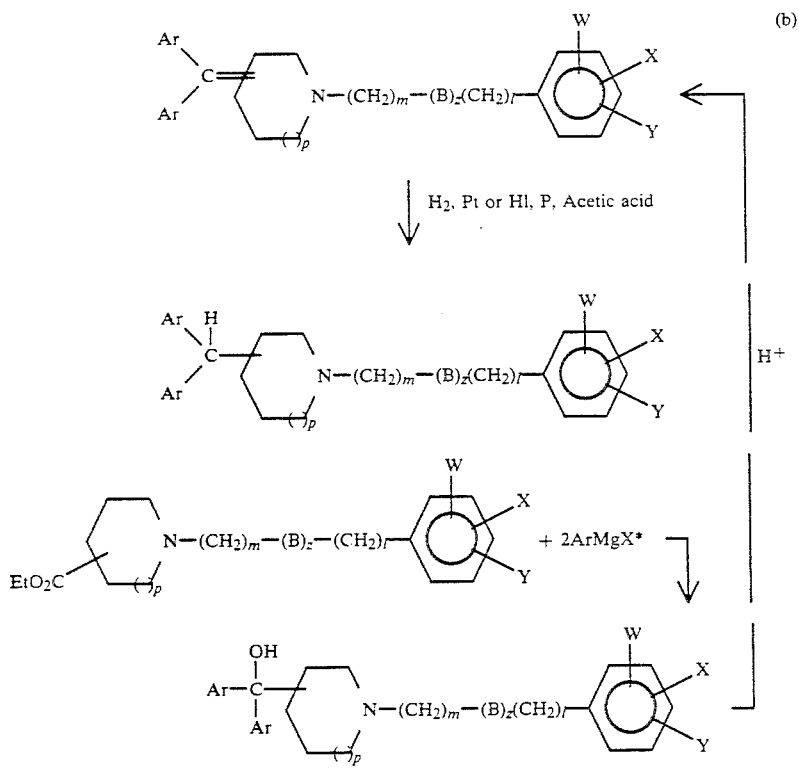
(b)
*X = halo
(R = Ar, n of (Q)n is zero)

-continued
Chart II
Alternate Methods of Preparation for Compounds of Formula I

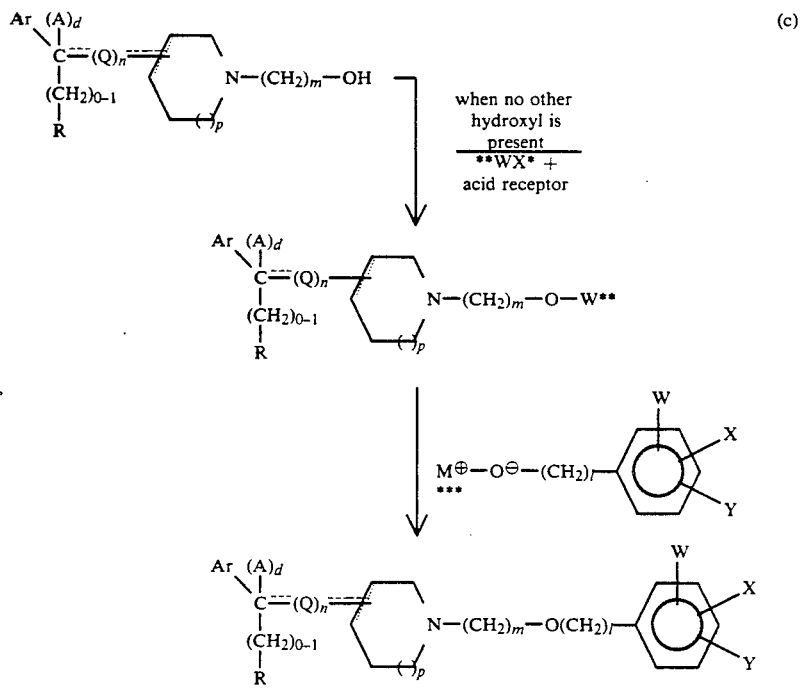

(c)

Footnotes:
*X = halo
**W = mesyl, tosyl, etc.
***M = Alkali-metal ion

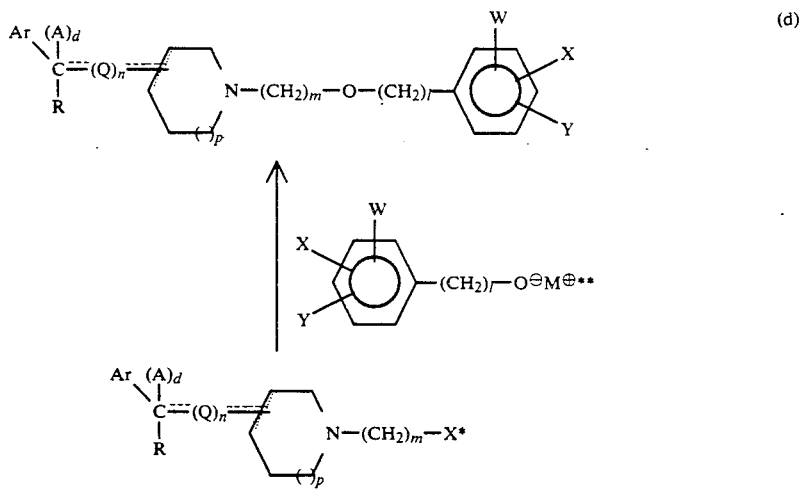

(d)

*X = halo
**M = Alkali-metal ion

To prepare an acid addition salt, the free base is reacted with the calculated amount of organic or inorganic acid in aqueous miscible solvent such as ethanol or isopropanol, with isolation by concentrating and/or cooling, or the base is reacted with an excess of the acid in aqueous immiscible solvent such as diethyl ether or isopropyl ether, with the desired salt separating directly. Exemplary of such organic salts are those formed with oxalic, maleic, fumaric, benzoic, ascorbic, pamoic, succinic, methanesulfonic, acetic, propionic, tartaric, citric, lactic, malic, citraconic, itaconic, hexamic, p-aminobenzoic, glutamic and stearic acid and the like. Exemplary of such inorganic salts are those formed with hydrochloric, hydrobromic, sulfuric, sulfamic, phosphoric and nitric acids.

To prepare quaternary salts the free base of a Formula I compound may be reacted with a loweralkyl halide, preferably methyl iodide or methylbromide, or may be reacted with a loweralkyl sulfate, preferably methyl sulfate.

If desired, the free base may be regenerated by partitioning the acid addition salt between an organic solvent such as methylene chloride and a weakly basic aqueous solution of, for example, sodium bicarbonate, and separating and evaporating the methylene chloride layer.

Precursors (Chemical Intermediates) used in the synthesis of compounds of Formula I are prepared in a number of ways as illustrated by the following 1 to 11 sets of equations which are also applicable to pyrrolidinyl and homopiperidinyl derivatives. (See also U.S. Pat. Nos. 3,922,276 and 3,956,296).

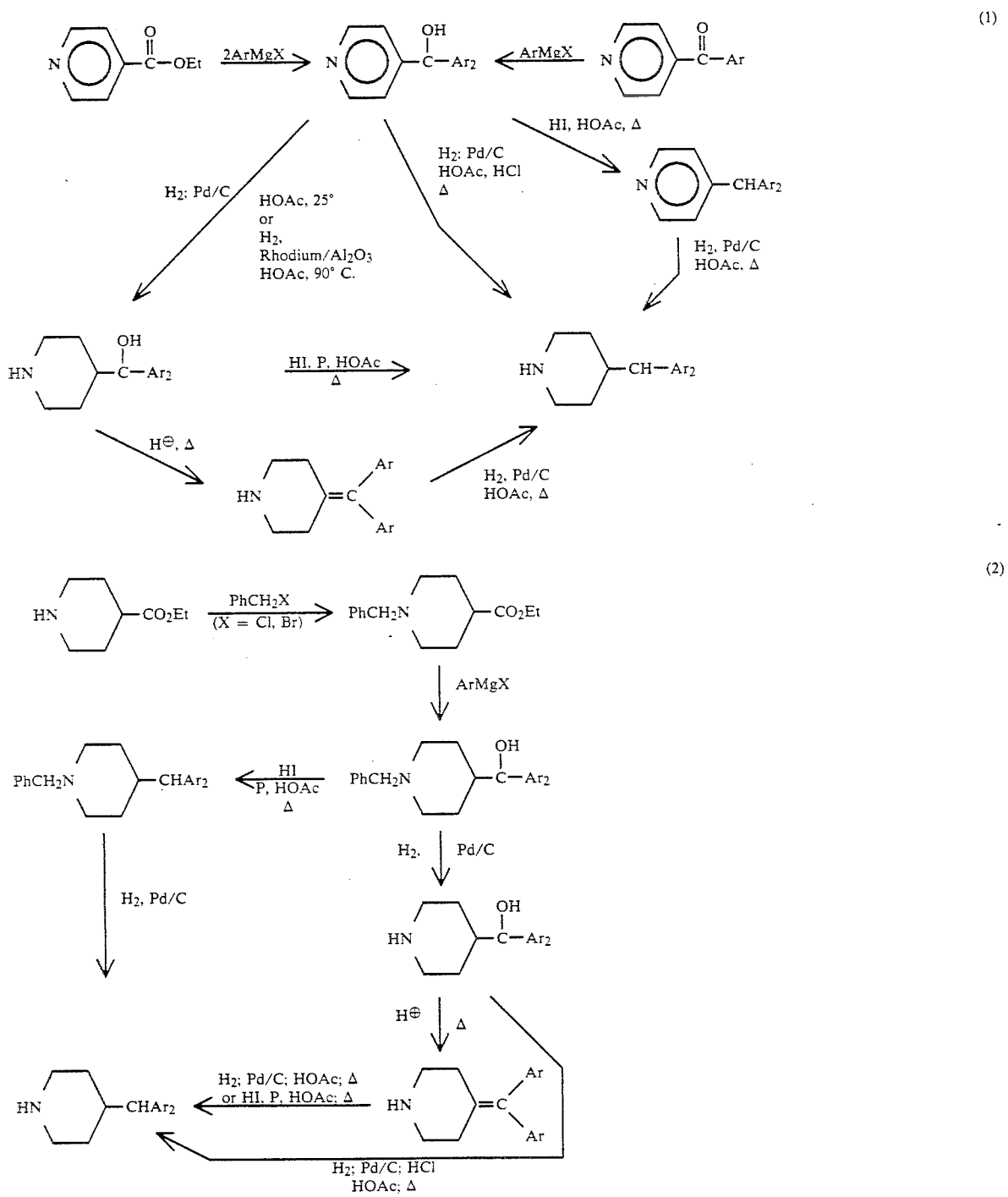

Ph = phenyl.

-continued
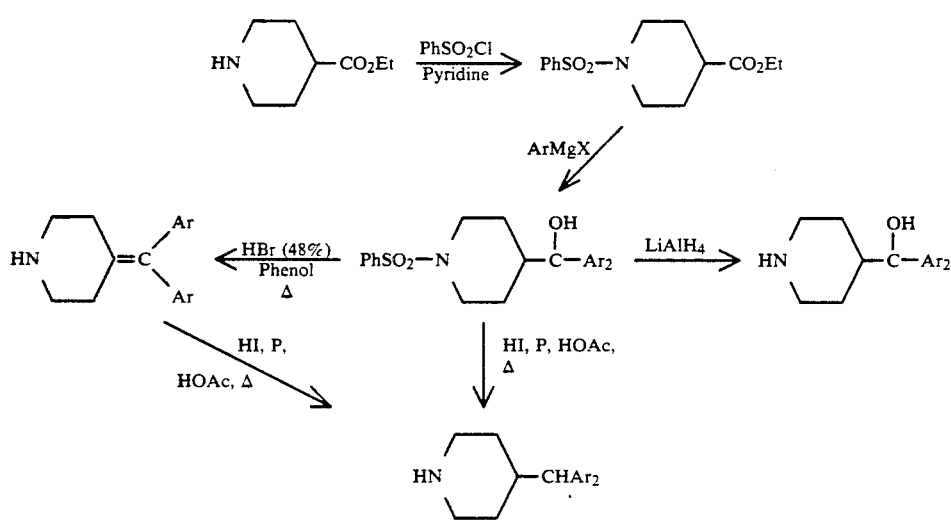
(3)
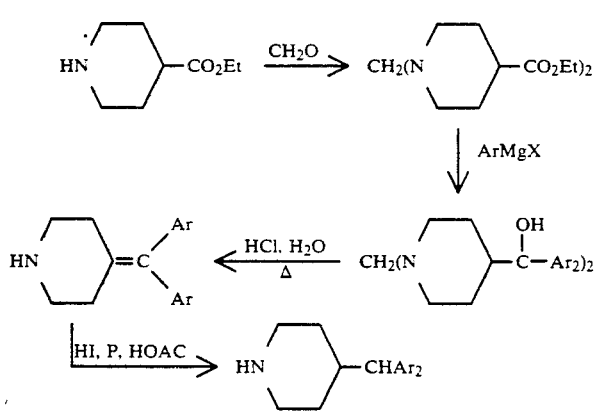
(4)
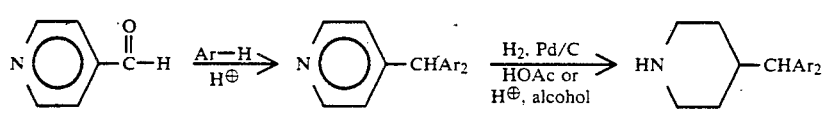
(5)
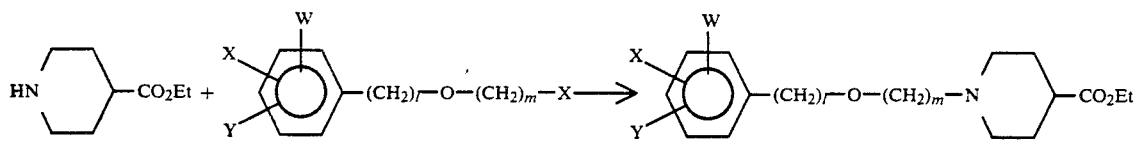
(6)
X = Cl, Br
Ph = phenyl.
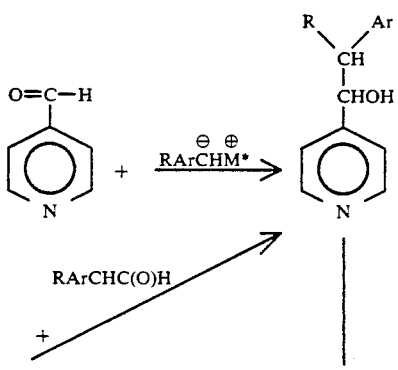
(7)

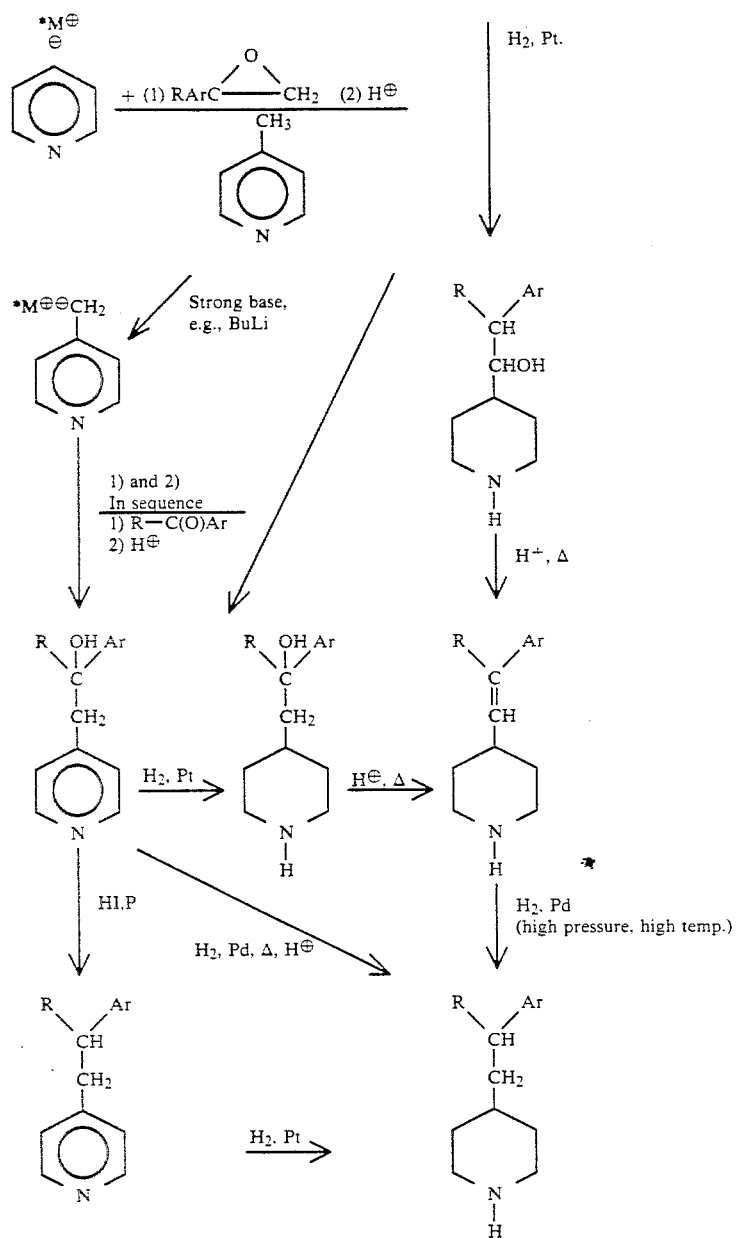
*M⊕ = Li⊕ or MgBr⊕
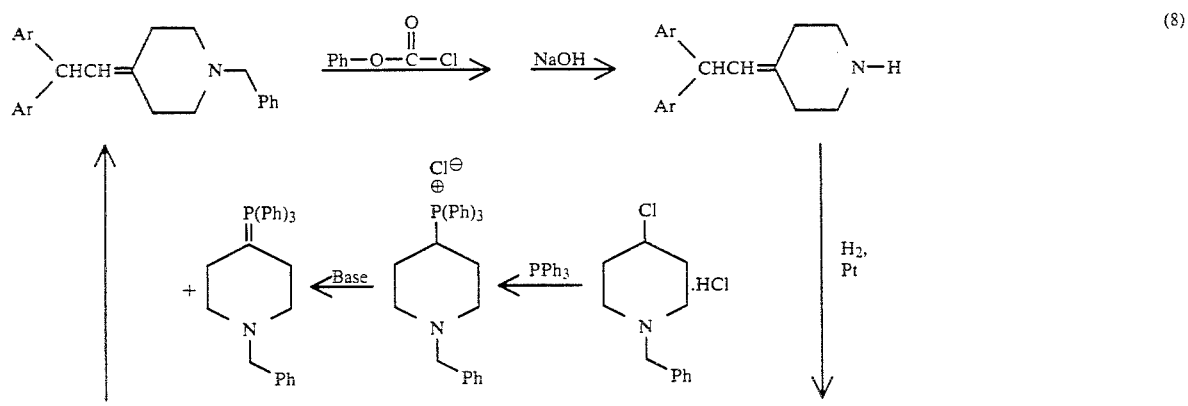
(8)

-continued
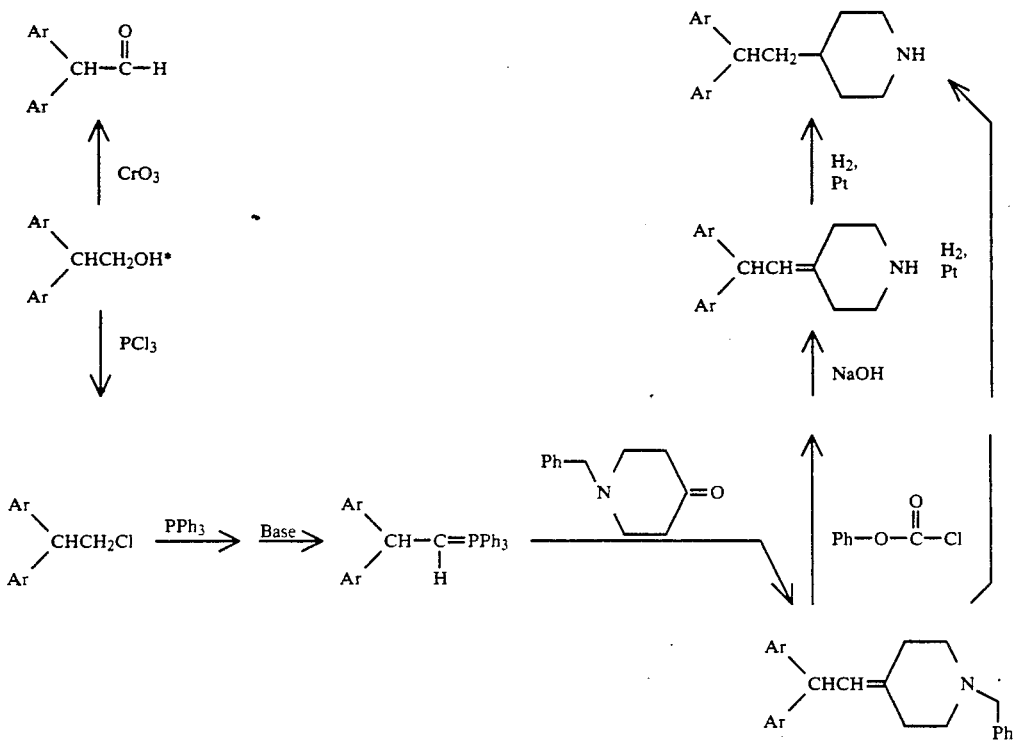
*Commercially available
Ph = phenyl
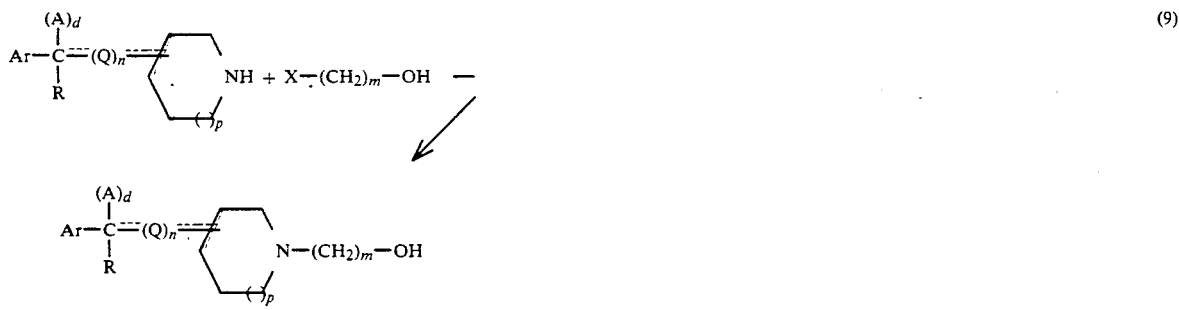
(9)
X = halo.
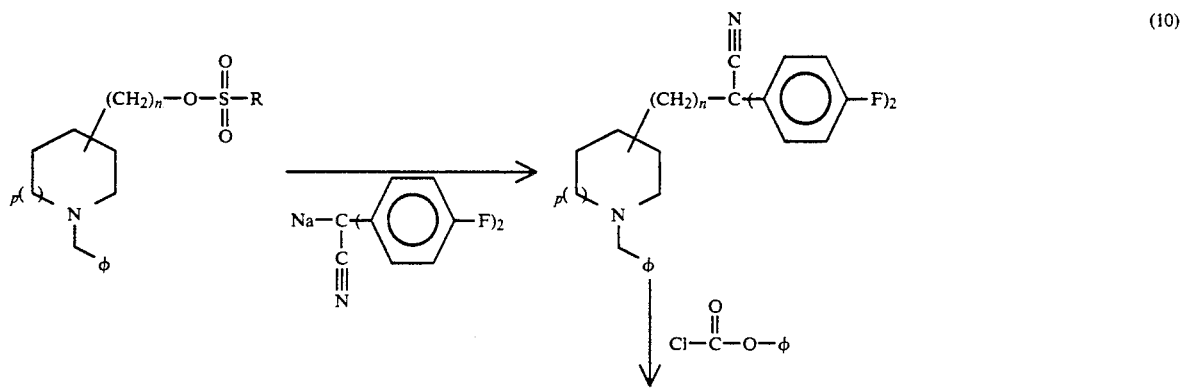
(10)

-continued
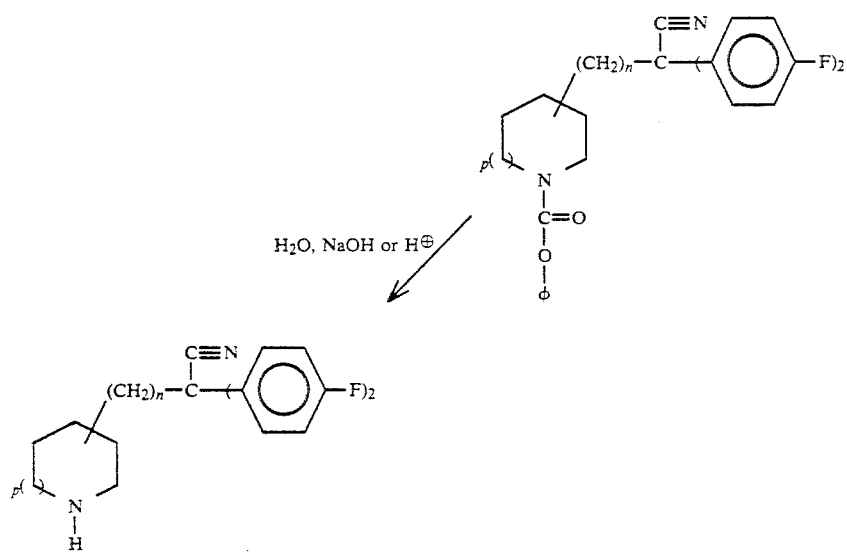
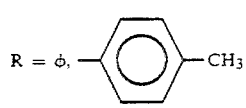
n = 0,1
φ = phenyl
(11)
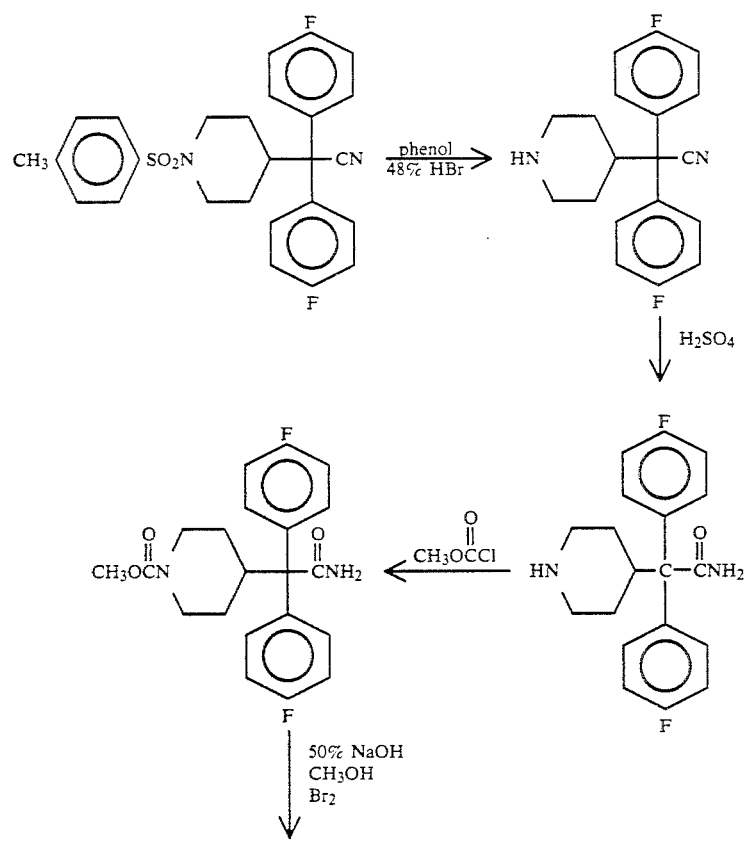

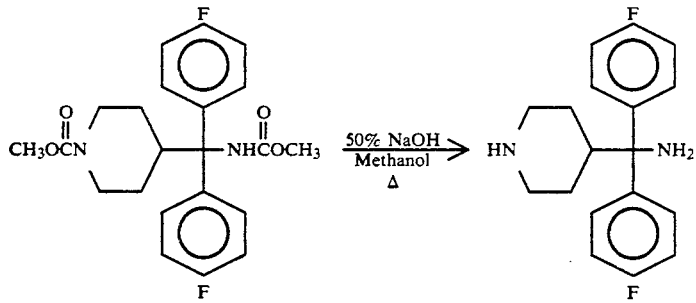

The following preparations and examples serve to illustrate the preferred embodiments of the present invention, but in no way should be construed to limiting the invention disclosed herein.

PREPARATION 1

1-(Phenylmethyl)-4-piperidinecarboxylic acid ethyl ester hydrochloride[1:1].

A mixture of 100 g (0.637 mole) of ethyl isonipecotate, 80.64 g (0.64 mole) of benzyl chloride and 67.84 g (0.64 mole) of sodium carbonate in 1 liter of absolute ethanol was heated at reflux for 8 hours and then was stirred at room temperature for 10 hours. The solvent was removed in vacuo, and the residue was partitioned between methylene chloride and sodium hydroxide solution. The methylene chloride phase was dried over magnesium sulfate, and the solvent was removed in vacuo to give the free base of the title compound as a liquid. The free base was converted to the hydrochloride, and the salt was recrystallized from ethanol-ether to give 89.33 g (49.7%) of the title compound as a white, crystalline solid, mp 154°-155° C.

Analysis: Calculated for $C_{15}H_{21}NO_2 \cdot HCl$: C, 63.48; H, 7.81; N, 4.94. Found: C, 63.07; H, 7.82; N, 4.91.

PREPARATION 2

α,α-bis-(4-Fluorophenyl)-1-(phenylmethyl)-4-piperidinemethanol

To a dry 2 liter round bottom flask containing magnesium turnings (6.08 g, 0.25 mole) and an iodine crystal in 600 ml of dry tetrahydrofuran (distilled from lithium aluminum hydride) and under an atmosphere of nitrogen was added, dropwise, a solution of 52.5 g (0.30 mole) of p-bromofluorobenzene in 125 ml of tetrahydrofuran. The temperature of the reaction mixture was kept below 10° C. by cooling in an ice-methanol bath. The mixture was stirred at room temperature for 1.5 hours. A solution of 1-(phenylmethyl)-4-piperidinecarboxylic acid ethyl ester (24.7 g, 0.1 mole) in tetrahydrofuran was added, and the mixture was stirred at room temperature for 17 hours. The reaction was poured into an icy, aqueous solution of ammonium chloride, and the resulting solution was extracted with methylene chloride. The methylene chloride solution was extracted with dilute sodium hydroxide and was dried (magnesium sulfate). The solvent was removed in vacuo to give an oil. This was crystallized from ether-hexane to give 19.87 g (51%) of the title compound, mp 113°-115° C.

Analysis: calculated for $C_{25}H_{25}F_2NO$: C, 76.31; H, 6.40; N, 3.56. Found: C, 76.24; H, 6.38; N, 3.50.

PREPARATION 3

α,α-Bis(4-fluorophenyl)-4-piperidinemethanol

A solution of 31.2 g (0.079 mole) of α,α-bis-(4-fluorophenyl)-1-(phenylmethyl)-4-piperidinemethanol in 400 ml of absolute ethanol was hydrogenated at 50 psi and 70° C. over 5% palladium on carbon over the weekend. The mixture was filtered and the filtrate was concentrated under reduced pressure to give a gum as residue. Trituration of the gum with methylene chloride gave a solid. The mixture was diluted with petroleum ether and the solid was collected by filtration, washed with petroleum ether, and dried to yield 22 g (92%) of the title compound as a white solid, mp 159.5°-160.6° C. (isopropyl ether/2-propanol).

Analysis: Calculated for $C_{18}H_{19}F_2NO$: C, 71.27; H, 6.31; N, 4.62. Found: C, 70.93; H, 6,71; N, 4.38.

PREPARATION 4

4-(3-Chloropropoxy)-3-methoxybenzoic acid methyl ester

A mixture of 100 g (0.549 mole) of methyl vanillate, 172.8 g (1.1 mole) of 1-bromo-3-chloropropane and 228 g (1.65 mole) of anhydrous potassium carbonate in 1 liter of acetone was heated at reflux for 20 hr. The mixture was cooled, filtered, and the filtrate concentrated to give a white solid as residue. The solid was triturated with petroleum ether, collected by filtration, and dried to yield 137.8 g (97%) of the title compound as a white powder, mp 104°-105° C. (2-propanol).

Analysis: Calculated for $C_{12}H_{15}ClO_4$: C, 55.71; H, 5.84. Found: C, 55.87; H, 5.94.

PREPARATION 5

4-[3-[4-[Bis(4-fluorophenyl)hydroxymethyl]-1-piperidinyl]propoxy]-3-methoxybenzoic acid methyl ester A mixture of α,α-bis(4-fluorophenyl)-4-piperidinemethanol (6.0 g, 0.02 mole), 4-(3-chloropropoxy)-3-methoxybenzoic acid methyl ester (5.4 g, 0.021 mole), anhydrous sodium carbonate (7.4 g, 0.07 mole), and potassium iodide (0.3 g) in 150 ml of dimethylformamide was heated on a steam bath for about 20 hr. The mixture was concentrated under reduced pressure, and the residue was partitioned between water and organic solvent (benzene). The organic layer was washed with water and brine and dried over sodium sulfate and eventually crystallized from 2-propanol to give the title compound as a white solid, mp 131°-132.5° C. (2-propanol).

Analysis: Calculated for $C_{30}H_{33}F_2NO_5$: C, 68.56; H, 6.33; N, 2.67. Found: C, 68.23; H, 6.35; N, 2.6.

PREPARATION 6

4-(3-Chloropropoxy)-3-methoxybenzeneacetic acid ethyl ester

A mixture of 50 g (0.238 mole) of ethyl homovanillate (98%), 75 g (0.476 mole) of 1-bromo-3-chloropropane and 98.7 g (0.71 mole) of anhydrous potassium carbonate in 1 liter of actone was heated at reflux for 24 hr. The mixture was filtered and the filtrate was concentrated under reduced pressure to give an oil which gradually crystallized to a semi-solid. The solid was recrystallized from ethyl ether-petroleum ether (30°-60° C.) to yield 44.4 g (65%) of the title compound as a white solid, mp 36°-38° C.

Analysis: Calculated for $C_{14}H_{19}ClO_4$: C, 58.64; H, 6.68. Found: C, 58.74; H, 6.74.

PREPARATION 7

4-[3-[4-[Bis(4-fluorophenyl)hydroxymethyl]-1-piperidinyl]propoxy]-3-methoxybenzeneacetic acid sodium salt hydrate [1:1:0.5]

A mixture of 3.0 g (0.01 mole) of α,α-bis(4-fluorophenyl)-4-piperidinemethanol, 2.9 g (0.01 mole) of 4-(3-chloropropoxy)-3-methoxybenzeneacetic acid ethyl ester, 5.3 g (0.05 mole) of anhydrous sodium carbonate and 0.3 g of potassium iodide in 150 ml of acetonitrile was heated at reflux temperature for 20 hr. The mixture was concentrated under reduced pressure and the residue partitioned between benzene and water. The benzene layer was washed with water and brine, dried over sodium sulfate, and concentrated under reduced pressure to give the ethyl ester of the title compound as a gum. The gum was converted to the hydrochloride with ethereal hydrogen chloride to give a white solid. The solid could not be recrystallized so it was partitioned between methylene chloride and a 5% sodium hydroxide solution. An emulsion resulted which was let stand for 2 months while the layers separated. During this time a solid precipitated. The mixture was filtered. The filter cake was recrystallized from ethyl acetate to yield 0.7 g (13%) of the title compound as a fluffy, white solid, mp 102°-112° C.

Analysis: Calculated for $C_{30}H_{32}F_2NNaO_5 \cdot 0.5H_2O$: C, 64.74; H, 5.98; N, 2.52. Found: C, 64.50; H, 5.97; N, 2.39.

PREPARATION 8

2-Chloro-1-(4-hydroxy-3-methoxyphenyl)ethanone

To a cooled (ice bath) stirred solution of 130.3 g (1.05 mole) of 2-methoxyphenol in 750 mL of carbon disulfide was continuously added 306.6 g (2.3 mole) of anhydrous aluminum chloride portionwise. The stirred, cooled mixture was then treated dropwise with 80 mL (113 g, 1.0 mole) of 2-chloroacetyl chloride. After the addition was completed, the mixture was heated at reflux temperature for 20 hr, cooled, and poured into a mixture of 2 kg of crushed ice and 200 ml of concentrated hydrochloric acid. The solid which gradually crystallized was washed with water and carbon disulfide and dried. The solid was recrystallized from isopropyl ether containing a few drops of 2-propanol to yield 128.3 g (64% yield) of the title compound, mp 102°-103° C.

Analysis: Calculated for $C_9H_9ClO_3$: C, 53.88; H, 4.52. Found: C, 53.87; H, 4.5.

PREPARATION 9

2-(Acetyloxy)-1-(4-hydroxy-3-methoxyphenyl)ethanone

To a slurry of 80.2 g (0.4 mole) of 2-chloro-1-(4-hydroxy-3-methoxyphenyl)ethanone in 576 ml of absolute ethanol and 24 ml of glacial acetic acid was added 73.6 g (0.75 mole) of potassium acetate, and the mixture was heated at reflux temperature for 1 hr. The mixture was cooled, filtered, and the filtrate concentrated to a gummy residue. The residue was triturated with four 200 ml portions of hot benzene. The combined extracts were washed with three 200 ml portions of saturated aqueous sodium bicarbonate solution and once with brine, dried over sodium sulfate, and concentrated to give a solid residue. The solid was recrystallized from benzene (with charcoal treatment) to yield 32.4 g (36% yield) of the title compound as a white solid, mp 115°-117° C.

Analysis: Calculated for $C_{11}H_{12}O_5$: C, 58.93; H, 5.39. Found: C, 59.01; H, 5.37.

PREPARATION 10

2-(Acetyloxy)-1-[4-(3-chloropropoxy)-3-methoxyphenyl]ethanone

A mixture of 31.5 g (0.14 mol) of 2-(acetyloxy)-1-(4-hydroxy-3-methoxyphenyl)ethanone, 44.1 g (0.28 mole) of 1-bromo-3-chloropropane and 58 g (0.42 mole) of anhydrous potassium carbonate in 1 liter of acetone was heated at reflux for 16 hr. The mixture was cooled, filtered, and the filtrate concentrated to give a solid residue. The solid was triturated with petroleum ether (30°-60° C.), collected by filtration and dried to yield 38.7 g (92%) of title compound as a pale-yellow solid. An analytical sample, mp 93°-96° C., was prepared from 2-propanol.

Analysis: Calculated for $C_{14}H_{17}ClO_5$: C, 55.91; H, 5.7. Found: C, 55.95; H, 5.71.

PREPARATION 11

2-(Acetyloxy)-1-[4-[3-[4-[bis(4-fluorophenyl)hydroxymethyl]-1-piperidinyl]propoxy]-3-methoxyphenyl]ethanone.

A mixture of 9.1 g (0.03 mole) of α,α-bis(4-fluorophenyl-4-piperidinemethanol, 9.0 g (0.03 mole) of 2-(acetyloxy)-1-[4-(3-chloro)-3-methoxyphenyl]ethanone, 10.6 g (0.1 mole) of anhydrous sodium carbonate and 0.6 g of potassium iodide in 200 ml of dimethylformamide was heated at reflux for about 20 hr and gave a solid residue. The solid was purified by column chromatography on 300 g of Florisil ®. Fractions eluted with 2.5-35% acetone in benzene were combined and concentrated to yield 11.8 g (69%) of the title compound as pale-yellow crystals. An analytical sample, mp 138°-140° C., was recrystallized from isopropyl ether-benzene.

Analysis: Calculated for $C_{32}H_{35}F_2NO_6$: C, 67.71; H, 6.22; N, 2.47. Found: C, 67.97; H, 6.26; N, 2.47.

PREPARATION 12

(4-Fluorophenyl)[1-(phenylsulfonyl)-4-piperidinyl]methanone

A mixture of 4-(4-fluorobenzoyl)piperidine hydrochloride (53.3, 0.219 mole and benzenesulfonyl chloride (44 g, 0.25 mole) in 500 ml of pyridine was stirred at room temperature overnight. The solvent was removed in vacuo, and the residue was partitioned between methylene chloride and dilute sodium hydroxide. The methylene chloride solution was extracted with dilute sulfuric acid and then was dried over magnesium sulfate. The volume was reduced to 400 ml, hexane was added and 39.2 g (50.6%) of the title compound was collected as a white, crystalline solid, mp 156.5°–158° C.

Analysis: Calculated for $C_{18}H_{18}FNO_3S$: C, 62.23; H. 5.22; N, 4.03. Found: C, 62.13; H, 5.20; N, 4.13.

PREPARATION 13

α-(3,4-Difluorophenyl)-α-(4-fluorophenyl)-1-(phenylsulfonyl)-4-piperidinemethanol A three-necked round bottom flask, equipped with a mechanical stirrer, flushed with nitrogen, and containing 3.74 g (0.154 mole) of magnesium turnings, was dried with a Bunsen burner. After the flask had cooled, 600 ml of tetrahydrofuran was added. To this mechanically stirred mixture was slowly added a solution of 29.4 g (0.152 mole) of 4-bromo-1,2-difluorobenzene in 50 ml of tetrahydrofuran. The mixture was stirred for 1 hour, and 45.11 g (0.13 mole) of (4-fluorophenyl)[1-(phenylsulfonyl)-4-piperidinyl]methanone was added as a solid. The solution was stirred at ambient temperatures for 3 hours and was poured into an icy aqueous solution of ammonium chloride. The aqueous mixture was extracted with methylene chloride, dried over magnesium sulfate, and the solvent was removed in vacuo. The residue was recrystallized from methylene chloridehexane to give 58.89 g (82.9%) of the title compound. A small sample was recrystallized from a mixture of methylene chloride-ether-hexane to give an analytically pure sample of the title compound, mp 97°–99° C.

Analysis: Calculated for $C_{24}H_{22}F_3NO_3S$: C, 62.46; H, 4.81; N, 3.04. Found: C, 62.63; H, 4.86; N, 3.02.

PREPARATION 14

4-[(3,4-Difluorophenyl)(4-fluorophenyl)methylene]-piperidine oxalate [1:1]

A mixture of 30.19 g (0.065 mole) of α-(3,4-difluorophenyl)-α-(4-fluorophenyl)-1-phenylsulfonyl-4-piperidinemethanol, 4.0 g (0.125 mole) of phosphorus and 160 ml of 47% hydrogen iodide in 400 ml of glacial acetic acid was heated at reflux for 52.5 hours. The solvent was removed in vacuo, and the residue was partitioned between methylene chloride and dilute sodium hydroxide. The methylene chloride solution was dried over sodium sulfate and was filtered through a sintered glass funnel (fine porosity), and the solvent was removed in vacuo. The residue was flash chromatographed (silica gel, elution with methanol and then with a 99/1 mixture of methanolammonium hydroxide) to give the non-salt forms of the title compound and the compound of Preparation 15. The solid title compound free base was converted to the oxalate to yield 0.47 g (0.24%) of a white solid, mp 195°–198° C. (methanol-ethyl ether).

Analysis: Calc. for $C_{18}H_{16}F_3N.C_2H_2O_4$: C, 61.07; H, 4.61; N, 3.56. Found: C, 60.88; H, 4.57; N, 3.57.

PREPARATION 15

4-[(3,4-Difluorophenyl)(4-fluorophenyl)methyl]piperidine oxalate hydrate [1:1:0.5]

The free base of the title compound was obtained as described in Preparation 14. The compound was converted to the oxalate salt and recrystallized from acetonitrile to give 5.64 g (21.5%) of a white solid, mp 78°–83° C.

Analysis: Calc. for $C_{18}H_{18}F_3N.C_2H_2O_4.0.5H_2O$: C, 59.40; H, 5.23; N, 3.46. Found: C, 59.58; H, 5.05; N, 3.48.

PREPARATION 16

4-[Bis(2,4-difluorophenyl)methyl]pyridine hydrochloride[1:1]

Sulfuric acid (40 ml) was cooled in an acetone-dry ice bath and 1,3-difluorobenzene (45.6 g, 0.4 mole) was added with stirring while maintaining a temperature of 0° C. 4-Pyridinecarboxaldehyde (21.4 g, 0.2 mole) was added dropwise while maintaining a temperature of 0° C. The reaction mixture was stirred until room temperature was reached, and the reaction mixture was then stirred overnight at 70° C. The reaction mixture was cooled to room temperature and made alkaline with ice/50% sodium hydroxide. The aqueous layer was extracted several times with chloroform, and the combined organic layers were back extracted with 5% sodium hydroxide. The chloroform layer was dried over sodium sulfate and filtered. The organic solvent was removed in vacuo to give a clear oil (28.30 g, 44.6%). A 1 g portion of the clear oil was dissolved in isopropanol and treated with ethereal hydrochloric acid. A white, crystalline solid formed and was separated. The solid was dried in vacuo overnight at 80° C. This furnished 0.97 g (39%) of white, crystalline solid, mp 218°–222° C.

Analysis: Calculated for $C_{18}H_{12}ClF_4N_4$: %C, 61.12; %H, 3.42; %N, 3.96. Found: %C, 61.00; %H, 3.32; %N, 3.94.

PREPARATION 17

4-[Bis(2,4-difluorophenyl)methyl]piperidine hydrochloride[1:1]

A mixture of 4-[bis(2,4-difluorophenyl)methyl]pyridine (23.84 g, 0.0752 mole) and 5% platinum on carbon (2.0 g) was subjected to hydrogenation for three days at 60° C. in 400 ml of glacial acetic acid containing 3 mL of concentrated hydrochloric acid. This reaction was carried out at a pressure of 45 psi and 13.5 pounds of hydrogen gas was consumed. The reaction mixture was cooled to room temperature and filtered. Solvent was removed by rotary evaporator. The residue obtained was dissolved in chloroform and extracted with 5% sodium hydroxide. The chloroform layer was dried over sodium sulfate and filtered. The chloroform was removed by rotary evaporator to give a dark residue (24.4 g, quantitative yield). A one-gram sample of this material was converted to the hydrochloride and the salt was recrystallized from methanol-diethyl ether. A white solid was obtained and dried in vacuo overnight at 80° C. This provided 1.06 g (95.2%) of the title compound as a white, crystalline solid, mp 215°–217° C.

Analysis: Calculated for $C_{18}H_{18}ClF_4N$: C, 60.09; H, 5.04; N, 3.89. Found: C, 59.77; H, 5.02; N, 3.87.

PREPARATION 18

α,α-Bis(3-fluorophenyl)-1-(phenylmethyl)-4-piperidinemethanol fumarate[1:1]

A Grignard solution was prepared from 100 g (0.57 mole) of 1-bromo-3-fluorobenzene and 12.2 g (0.5 mole) of magnesium chips in 750 ml dry tetrahydrofuran (THF). The solution was treated with a solution of 45.8 g (0.185 mole) of 1-(phenylmethyl)-4-piperidinecarboxylic acid ethyl ester in 250 ml of dry THF, and the mixture was stirred at ambient temperature overnight. The solution was poured into 2.5 liters of a saturated ammonium chloride solution, and the layers were separated. The aqueous layer was extracted once with 500 ml of methylene chloride and twice with 250 ml of methylene chloride. The combined organic layers were washed successively with 250 ml of water, 250 ml of a 4% sodium hydroxide solution, 250 ml of water, and 250 ml of brine, dried over sodium sulfate and concentrated to give a glass as residue. The glass was dissolved in 2-propanol and converted to the fumaric acid salt. The solid was collected by filtration and dried to yield 85 g (90%) of the title compound as a white solid. An analytical sample, mp 212°-214° C. (dec), was recrystallized from acetonitrile-water.

Analysis: Calculated for $C_{29}H_{29}F_2NO_5$: C, 68.36; H, 5.74; N, 2.75. Found: C, 68.46; H, 5.74; N, 2.83.

PREPARATION 19

α,α-Bis(3-fluorophenyl)-4-piperidinemethanol

A solution of 39.3 g (0.1 mole) of α,α-bis(3-fluorophenyl)-1-(phenylmethyl)-4-piperidinemethanol in 750 ml of absolute ethanol was hydrogenated over palladium on carbon in a Parr apparatus at 50 psi and 60° C. for 3.5 days. The mixture was cooled and filtered through Celite ®. The filtrate was concentrated, and the residue was dissolved in ethyl ether and filtered through cotton to remove some insoluble material. The filtrate was concentrated to give a gum which crystallized when triturated with petroleum ether (30°-60° C.). The solid was collected by filtration and dried to yield 27.9 g (92%) of the title compound as a white solid. An analytical sample, mp 117°-118° C., was recrystallized from isopropyl ether/2-propanol.

Analysis: Calculated for $C_{18}H_{19}F_2NO$: C, 71.27; H, 6.31; N, 4.62. Found: C, 71.24; H, 6.27; N, 4.66.

PREPARATION 20

4-Fluoro-α-(4-fluorophenyl)benzeneacetonitrile

4-Fluorophenylacetonitrile (70.0 g, 62.2 ml, d=1.126, 0.518 mole) was heated to 120° C. Bromine (83.0 g, 26.6 ml, d=3.119, 0.525 mole) was added dropwise over 1 hour while maintaining the temperature at 120° C. The solution was stirred for 0.5 hour at 120° C. and then flushed vigorously with nitrogen for 0.75 hour (solution A).

In a separate 2-liter flask was placed aluminum chloride (85.0 g, 0.644 mole). Fluorobenzene (200 g, 2.08 mole, d=1.024, 195.3 ml) was added dropwise with stirring over ½ hour while flushing with nitrogen (Mixture B).

Solution A was added dropwise to mixture B at room temperature. The temperature rose to 50° C. The reaction mixture was stirred at this temperature for 0.3 hour. The temperature was raised to 70° C. and maintained there for 0.3 hour, whereupon, a portion of the reaction mixture shot out of its flask.

Remains of the reaction mixture were combined and added to a mixture of ice and 75 ml of concentrated hydrochloric acid. The aqueous phase was extracted several times with chloroform. The solvent layer was dried, filtered, and solvent removed to give a green solid. The solid was recrystallized from 2-propanol; the solid was washed with cold 2-propanol twice and dried in vacuo at 55° C. overnight. This produced 29.72 g (25.1% yield) of light-yellow solid, mp 62°-63.5° C.

Analysis: Calculated for $C_{14}H_9F_2N$: C, 73.36; H, 3.96; N, 6.11. Found: C, 73.55; H, 3.88; N, 6.1.

PREPARATION 21

4-Methylphenylsulfonic Acid Ester with 1-[(4-Methylbenzene)sulfonyl]-4-piperidinol A solution of 1.63 g (0.0161 mole) of 4-hydroxypiperidine and 13.91 g (0.0732 mole) of tosyl chloride in 80 ml of pyridine was stirred at 25° C. overnight. The mixture was quenched in 200 ml of water, and the aqueous mixture was extracted with several portions of methylene chloride. The methylene chloride solution was extracted with several portions of sulfuric acid solution and 1M sodium hydroxide solution and then was dried over magnesium sulfate. The solvent was removed in vacuo to give a solid. This was recrystallized from methylene chloride-diethyl ether to give 4.82 g (73.3%) of the product, mp 140.5°-141° C.

Analysis: Calculated for $C_{19}H_{23}NO_5S_2$: C, 55,73; H, 5.66; N, 3.42. Found: C, 55.60; H, 5.64; N, 3.39.

PREPARATION 22

α,α-Bis(4-fluorophenyl)-1-[(4-methylphenyl)sulfonyl]-4-piperidineacetonitrile

The sodium salt of 4-fluoro-α-(4-fluorophenyl)benzeneacetonitrile was prepared in dimethyl sulfoxide from 4-fluoro-α-(4-fluorophenyl)benzeneacetonitrile (free base, 28.0 g, 0.12 mole) and sodium hydride (60%, 4.90 g, 0.12 mole). The salt was stirred for 1 hr at room temperature. Next, 4-methylphenylsulfonic acid ester with 1-[(4-methylbenzene)sulfonyl]-4-piperidinol (50.0 g, 0.12 mole) was added over five minutes in solid form while stirring under nitrogen. The resulting solution was stirred 15 hours at 65° C. and then allowed to stand at room temperature for 72 hours. The solution was concentrated to dryness, the residue was dissolved in chloroform, and the resulting solution was extracted several times with 5% sodium hydroxide. The chloroform layer was dried over anhydrous sodium sulfate and filtered, and solvent was removed to give 111.36 g of solid. The solid was triturated with isopropyl ether and placed in the freezer. After washing the solid several times with isopropyl ether, 55.41 g of white solid was obtained. A 3-g sample was then triturated with 50-50 (v/v) hot isopropyl alcohol/methyl alcohol and placed in the freezer. The white solid collected was washed with isopropyl ether and dried in vacuo at 80° C. overnight. This produced 2.28 g (74% yield) of white, crystalline product, mp. 190°-191° C.

Analysis: Calculated for $C_{26}H_{24}F_2N_2O_2S$: C, 66.94; H, 5.18; N, 6.00. Found: C, 66.92; H, 5.17; N, 5.99.

PREPARATION 23

α,α-Bis(4-fluorophenyl)-4-piperidineacetonitrile oxalate diethyl ether [1:1:0.5]

A solution of α,α-bis(4-fluorophenyl)-1-[(4-methylphenyl)sulfonyl]-4-piperidineacetonitrile (52.41 g 0.11 mole) in 200 ml of 48% hydrobromic acid with phenol (50.0 g, 0.53 mole) was heated at reflux for 3.5 hours. The reaction mixture was cooled to room temperature and then made alkaline with ice/50% sodium hydroxide. The alkaline phase was extracted several times with chloroform. The chloroform layer was back extracted with 5% sodium hydroxide. The chloroform layer was dried over anhydrous sodium sulfate and filtered, and solvent was removed to give 34.24 g of dark-brown oil.

The oil was converted to the oxalate and the salt was recrystallized from methanol-diethyl ether. The white solid obtained was dried in vacuo overnight at 80° C. This produced 34.24 g (69.3% yield) of white, crystalline product, mp 124°-127° C.

Analysis: Calc. for $C_{19}H_{18}F_2N_2 \cdot C_2H_2O_4 \cdot 0.5C_4H_{10}O$: C, 62.86; H, 5.73; N, 6.37. Found: C, 62.30; H, 5.78; N, 6.17.

PREPARATION 24

α,α-Bis(4-fluorophenyl)-1-[(4-methylphenyl)sulfonyl]-3-pyrrolidineacetonitrile

The sodium salt of 4-fluoro-α-(4-fluorophenyl)benzeneacetonitrile was prepared in dimethyl sulfoxide from 4-fluoro-α-(4-fluorophenyl)benzeneacetonitrile (11.60 g, 0.05 mole) and sodium hydride (60%, 2.02 g, 0.05 mole). Next 1-[(4-methylphenyl)sulfonyl]-3-pyrrolidinol (4-methylphenyl)sulfonate ester (20.0 g, 0.0506 mole) in 200 ml of dimethyl sulfoxide was added. The solution was stirred overnight at 55° C. The solvent was then removed. A dark-brown oil was obtained and dissolved in chloroform. The organic layer was extracted with 1N sulfuric acid and 5% sodium hydroxide. The chloroform layer was dried over sodium sulfate and filtered; solvent was removed to give a dark-brown oil. The oil was triturated with 2-propanol and placed in the freezer over the weekend. A brown solid was separated by filtration (18.33 g). A one gram sample of the solid was recrystallized from 2-propanol. A light-brown solid was separated and dried in vacuo overnight at 80° C. in the presence of phosphorus pentoxide. This process furnished 0.57 g (46% based on aliquot taken) of light-brown solid, mp 181°-183° C.

Analysis: Calculated for $C_{25}H_{22}F_2N_2S$: C, 66.36; H, 4.90; N, 6.19. Found: C, 65.80; H, 4.91; N, 6.03.

PREPARATION 25

α,α-Bis(4-fluorophenyl)-3-pyrrolidineacetonitrile oxalate hydrate [1:1:0.5]

A mixture of α,α-bis(4-fluorophenyl)-1-[(4-methylphenyl)sulfonyl]-3-pyrrolidineacetonitrile (16.6 g, 0.0367 mole), phenol (50 g, 0.53 mole) and 300 ml of 48% hydrobromic acid was heated at reflux for two hours. The reaction mixture was cooled to room temperature and made alkaline with ice/50% sodium hydroxide. The aqueous layer was extracted with chloroform. The chloroform layer was back extracted with 5% sodium hydroxide, dried over sodium sulfate and filtered, and solvent was removed to produce a dark brown oil. The dark-brown oil was dissolved in chloroform and extracted with 1N sulfuric acid. This acidic layer was discarded. The chloroform layer was extracted with base, and the solvent was removed to give a dark brown oil. This oil was converted to the oxalate, and the salt was recrystallized from methanol-diethyl ether. A white solid was isolated and dried in vacuo overnight at 80° C. This produced 7.17 g (49%) of off-white solid, mp 88.5°-90° C.

Analysis: Calculated for $C_{18}H_{16}F_2N \cdot C_2H_2O_4 \cdot 0.5H_2O$: C, 60.45; H, 4.82; N, 7.05. Found: C, 60.52; H, 4.56; N, 7.01.

PREPARATION 26

4-Hydroxy-3-methoxy-α-oxobenzeneacetic acid ethyl ester

To a cool (ice bath), stirring solution of 130.3 g (1.05 mole) of 2-methoxyphenol in 705 ml of carbon disulfide is cautiously added portionwise 306.6 g (2.3 mole) of anhydrous aluminum chloride. The mixture is then treated dropwise with 136.5 g (1.0 mole) of ethyl oxalyl chloride. After the addition is complete, the mixture is heated at reflux for 20 hr, cooled and poured into a mixture of 2 kg of crushed ice and 200 ml of concentrated hydrochloric acid. Sodium chloride is added and a solid precipitates. The solid is collected by filtration and is dried to give the title compound.

PREPARATION 27

4-(3-Chloropropoxy)-3-methoxy-α-oxobenzeneacetic acid ethyl ester

A mixture of 1 mole of 4-hydroxy-3-methoxy-α-oxobenzeneacetic acid ethyl ester, 2 mole of 1-bromo-3-chloropropane and 3 mole of anhydrous potassium carbonate in 3 liters of acetone is heated at reflux for 20 hr. The mixture is cooled, filtered and the filtrate concentrated to give a solid residue. The solid is triturated with petroleum ether (30°-60° C.), collected by filtration and dried to give the title compound.

PREPARATION 28

When in the procedure of Preparation 7 and substituting the following for α,α-bis(4-fluorophenyl)-4-piperidinemethanol:

a. 4-[(3,4-difluorophenyl)(4-fluorophenyl)methylene]-piperidine,
b. 4-[(3,4-difluorophenyl)(4-fluorophenyl)methyl]-piperidine,
c. 4-[bis(2,4-difluorophenyl)methyl]piperidine,
d. α,α-bis(3-fluorophenyl)-4-piperidinemethanol
e. α,α-bis(4-fluorophenyl)-4-piperidineacetonitrile, and
f. α,α-bis(4-fluorophenyl)-3-pyrrolidineacetonitrile there are obtained the following ethyl esters:

a. 4-[3-[4-[(3,4-difluorophenyl)(4-fluorophenyl)methylene]-1-piperidinyl]propoxy]-3-methoxybenzeneacetic acid ethyl ester,
b. 4-[3-[4-[(3,4-difluorophenyl)(4-fluorophenyl)methyl]-1-piperidinyl]propoxy]-3-methoxybenzeneacetic acid ethyl ester,
c. 4-[3-[4-[bis(2,4-difluorophenyl)methyl]-1-piperidinyl]propoxy]-3-methoxybenzeneacetic acid ethyl ester,
d. 4-[3-[4-[bis(3-fluorophenyl)hydroxymethyl]-1-piperidinyl]propoxy]-3-methoxybenzeneacetic acid ethyl ester,
e. 4-[3-[4-[bis(4-fluorophenyl)cyanomethyl]-1-piperidinyl]propoxy]-3-methoxybenzeneacetic acid ethyl ester, and
f. 4-[3-[3-[bis(4-fluorophenyl)cyanomethyl]-1-pyrrolidinyl]propoxy]-3-methoxybenzeneacetic acid ethyl ester which may later be converted to their respective benzeneacetic acid sodium salts if desired.

PREPARATION 29

When in the procedure of Preparation 5, and substituting the following for α,α-bis(4-fluorophenyl)-4-piperidinemethanol:

a. 4-[(3,4-difluorophenyl)(4-fluorophenyl)methylene]-piperidine,
b. 4-[(3,4-difluorophenyl)(4-fluorophenyl)methyl]-piperidine,
c. 4-[bis(2,4-difluorophenyl)methyl]piperidine,
d. α,α-bis(3-fluorophenyl)-4-piperidinemethanol
e. α,α-bis(4-fluorophenyl)-4-piperidineacetonitrile, and f. α,α-bis(4-fluorophenyl)-3-pyrrolidineacetonitrile
there are obtained the following:
a. 4-[3-[4-[(3,4-difluorophenyl)(4-fluorophenyl)methylene]-1-piperidinyl]propoxy]-3-methoxybenzoic acid methyl ester,
b. 4-[3-[4-[(3,4-difluorophenyl)(4-fluorophenyl)methyl]-1-piperidinyl]propoxy]-3-methoxybenzoic acid methyl ester,
c. 4-[3-[4-[bis(2,4-difluorophenyl)methyl]-1-piperidinyl]propoxy]-3-methoxybenzoic acid methyl ester,
d. 4-[3-[4-[bis(3-fluorophenyl)methyl]hydroxymethyl]-1-piperidinyl]propoxy]-3-methoxybenzoic acid methyl ester,
e. 4-[3-[4-[bis(4-fluorophenyl)cyanomethyl]-1-piperidinyl]propoxy]-3-methoxybenzoic acid methyl ester,
f. 4-[3-[3-[bis(4-fluorophenyl)cyanomethyl]-1-pyrrolidinyl]propoxy]-3-methoxybenzoic acid methyl ester,

PREPARATION 30

When in the procedure of preparation 11 and substituting the following for α,α-bis(p-fluorophenyl)-4-piperidinemethanol:
a. 4-[(3,4-difluorophenyl)(4-fluorophenyl)methylene]-piperidine,
b. 4-[(3,4-difluorophenyl)(4-fluorophenyl)methyl]-piperidine,
c. 4-[bis(2,4-difluorophenyl)methyl]piperidine,
d. α,α-bis(3-fluorophenyl)-4-piperidinemethanol
e. α,α-bis(4-fluorophenyl)-4-piperidineacetonitrile, and
f. α,α-bis(4-fluorophenyl)-3-pyrrolidineacetonitrile
there are obtained:
a. 2-(acetyloxy)-1-[4-[3-[4-[(3,4-difluorophenyl)(4-fluorophenyl)methylene]-1-piperidinyl]propoxy]-3-methoxyphenyl]ethanone,
b. 2-acetyloxy-1-[4-[3-[4-[(3,4-difluorophenyl)(4-fluorophenyl)methyl]-1-piperidinyl]propoxy]-3-methoxyphenyl]ethanone,
c. 2-acetyloxy-1-[4-[3-[4-[bis(2,4-difluorophenyl)methyl]-1-piperidinyl]propoxy]-3-methoxyphenyl]ethanone,
d. 2-(acetyloxy)-1-[4-[3-[4-[bis(3-fluorophenyl)hydroxymethyl]-1-piperidinyl]propoxy]-3-methoxyphenyl]ethanone
e. 1-[3-[4-(2-acetyl-1-oxoethyl)-2-methoxyphenoxy]propyl]-α,α-bis(4-fluorophenyl)-4-piperidineacetonitrile
f. 1-[3-[4-(2-acetyl-1-oxoethyl)-2-methoxyphenoxy]propyl]-α,α-bis(4-fluorophenyl)-3-pyrrolidineacetonitrile.

PREPARATION 31

4-Diphenylmethylenepiperidine

A solution of 7.0 g of 1-acetyl-4-diphenylhydroxymethylpiperidine in 30 ml of absolute alcohol and 76 ml of concentrated hydrochloric acid was heated at reflux for seven hours, cooled and made basic with 50% sodium hydroxide. The oil which separated was extracted with benzene, and the combined extracts washed with water. After being dried over magnesium sulfate, the solvent was evaporated at reduced pressure. The residual oil which crystallized on cooling was recrystallized twice from petroleum ether to give 4.0 g (73.0%) of white crystals, mp 85°–86° C.

Analysis: Calculated for C$_{18}$H$_{19}$N: C, 86.70; H, 7.68; N, 5.62. Found: C, 86.70; H, 7.83; N, 5.73.

PREPARATION 32

1-(Phenylsulfonyl)-4-piperidinecarboxylic acid ethyl ester

To a solution of 10.1 g (0.0642 mole) of ethyl isonipecotate in 300 ml of pyridine and cooled in an ice bath was added 13.2 g (0.075 mole) of benzenesulfonyl chloride. The mixture was stirred for 2 hours at room temperature, and the solvent was removed in vacuo. The residue was partitioned between methylene chloride and dilute sodium hydroxide. The methylene chloride solution was dried over magnesium sulfate, and the solvent was removed in vacuo to give a solid. This was recrystallized from ethanol-ether to give 4.59 g (24%) of crystalline solid, mp 85°–86.5° C.

Analysis: Calculated for C$_{14}$H$_{19}$NO$_4$S: C, 56.55; H, 6.44; N, 4.71. Found: C, 56.53; H, 6.55; N, 4.67.

In another preparation, 100 g (0.634 mole) of ethyl isonipecotate and 130.4 g (0.74 mole) of benzenesulfonyl chloride were reacted by the above procedure for 4.5 hr to give the title product in 78% yield.

PREPARATION 33

α,α-Bis(4-fluorophenyl)-1-(phenylsulfonyl)-4-piperidinemethanol

To a suspension of 33.78 g (1.39 mole) of magnesium turnings in 1 liter of tetrahydrofuran (dried over molecular sieves 5A) under an atmosphere of nitrogen and cooled in an ice bath was added dropwise a solution of 243.25 g (1.39 mole) of p-bromofluorobenzene in 150 ml of tetrahydrofuran. The mixture was stirred for 2 hr after the addition was completed. To this mixture was added 103 g (0.346 mole) of 1-(phenylsulfonyl)-4-piperidinecarboxylic acid ethyl ester as a solid, and the solution was stirred at ambient temperature for 5 hr. The reaction mixture was poured into an icy aqueous solution of ammonium chloride. The phases were separated, and the solvent was removed in vacuo from the organic phase. The residue was partitioned between methylene chloride and dilute sodium hydroxide. The methylene chloride solution was dried over magnesium sulfate and was reduced in vacuo to ≈1 liter volume. The title compound was obtained by adding hexane and cooling, recrystallizing the precipitate from ethyl acetate and hexane and drying the solid under high vacuum at 130° C. for 45 min at which time the product had partially melted, mp 142.5°–144° C.

Analysis: Calculated for C$_{24}$H$_{23}$F$_2$NO$_3$S: C, 65.00; H, 5.23; N, 3.16. Found: C, 65.21; H, 5.30; N, 3.1.

PREPARATION 34

4-[Bis(4-fluorophenyl)methylene]-1-(phenylsulfonyl)-piperidine

A solution of 5.23 g (0.0118 mole) of α,α-bis(4-fluorophenyl)-1-(phenylsulfonyl)-4-piperidinemethanol in 100 ml of acetic acid and 20 ml of 2M sulfuric acid was heated at reflux for 2.5 hours and then poured over ice. The mixture was made basic with 50% sodium hydroxide, and the basic mixture was extracted with methylene chloride. The methylene chloride solution was dried (anhydrous sodium sulfate), and the solvent was removed in vacuo. The residue was recrystallized from ether-hexane to give 3.23 g (64.4%) of white crystalline solid, mp 90°–92.5° C.

Analysis: Calculated for $C_{24}H_{21}F_2NO_2S$: C, 67.75; H, 4.98; N, 3.29. Found: C, 67.73; H, 5.00; N, 3.21.

PREPARATION 35

4-[Bis(4-fluorophenyl)methylene]piperidine hydrobromide [1:1]

A mixture of 164 g (0.342 mole) of α,α-bis(4-fluorophenyl)-1-(phenylsulfonyl)-4-piperidinemethanol and 80 g (0.85 mole) of phenol in 700 ml of 48% hydrobromic acid was heated at reflux for 7 hr and then was stirred at room temperature for 9 hr. The hydrobromic acid solution was decanted from a gum in the bottom of the reaction flask. The gum was triturated with ~1 liter of ether, and a tan solid formed. The solid was washed with several portions of ether and was dried under high vacuum to give 9.13 g (73%) of slightly impure title product, mp 211°-215° C. A small sample of this solid was recrystallized from methanol to give an analytically pure sample as a crystalline solid, mp 216°-218° C.

Analysis: Calculated for $C_{18}H_{17}F_2N\cdot HBr$: C, 59.03; H, 4.95; N, 3.82. Found: C, 58.96; H, 4.98; N, 3.76.

PREPARATION 36

4-[Bis(4-fluorophenyl)methyl]piperidine fumarate hydrate [1:0.5:0.5]

A mixture of 30.6 g (0.99 mole) of phosphorous and 15.1 g (0.059 mole) of iodine in 90 ml of glacial acetic acid was stirred for 20 min at room temperature. A mixture of 6 ml of water, 70 ml of methanesulfonic acid, 56.19 g (0.197 mole) of 4-[bis(4-fluorophenyl)methylene]piperidine and 110 ml of glacial acetic acid was added, and the mixture was heated at reflux for 7 hr. The solvent was removed in vacuo, and the resulting viscous liquid was poured over ice. The icy mixture was made basic with 50% sodium hydroxide, and the basic suspension was extracted with methylene chloride. The methylene chloride solution was extracted with an aqueous solution of sodium thiosulfate and was dried over anhydrous sodium sulfate, and the solution was filtered through Celite ®. The solvent was removed in vacuo to give a gum. The gum was dissolved in 400 ml of hot methanol, and 4.25 g of an unknown tan solid was collected from the warm solution. Fumaric acid (22 g, 0.19 mole) was added to the methanolic solution followed by the addition of ether. A white precipitate was collected to give 22.55 g (32%) of crystalline solid, mp 208°-209° C.

Analysis: Calculated for $C_{18}H_{19}F_2N\cdot0.5C_4H_4O_4\cdot0.5H_2O$: C, 67.78; H, 6.26; N, 3.95. Found: C, 67.86; H, 6.12; N, 3.81.

PREPARATION 37

4-[α-(p-Fluorophenyl)-α-phenyl]methylpiperidine hydrochloride [1:1]

This compound was prepared as described in U.S. Pat. No. 4,032,642 by hydrogenation of α-(p-fluorophenyl)benzylidinepiperidine over palladium charcoal catalyst, mp 81°-82° C.

Analysis: Calculated for $C_{18}H_{21}ClFN$: C, 70.69; H, 6.92; N, 4.58. Found: C, 70.69; H, 6.93; N, 4.52.

PREPARATION 38

4-(Diphenylmethyl)pyridine

A mixture of 99 g (0.379 mole) of diphenyl-4-pyridylmethanol, 50 ml of concentrated hydrochloric acid, 200 ml of 57% hydroiodic acid and 200 ml of glacial acetic acid was heated at reflux for 4.5 hr and then was stirred at room temperature for 12 hr. The reaction mixture was poured over ice and was made basic with 50% sodium hydroxide. An aqueous solution of sodium thiosulfate was added, and the mixture was extracted with methylene chloride. The methylene chloride solution was dried over magnesium sulfate, and the solvent was removed in vacuo. The residue was recrystallized from a mixture of methylene chloride-ether-hexane to give two crops of crystalline solids: crop I, 40.87 g (44.0%), mp 124°-126° C.; crop II, 25.38 g (27.3%), mp 123°-125° C. Analysis of the mixture of the crops I and II was as follows:

Analysis: Calculated for $C_{18}H_{15}N$: C, 88.13; H, 6.16; N, 5.71. Found: C, 87.67; H, 6.01; N, 5.56.

PREPARATION 39

4-(Diphenylmethyl)piperidine hydrochloride [1:1]

A mixture of 62.69 g (0.256 mole) of 4-(diphenylmethyl)pyridine and 6.4 g of 10% palladium on carbon (0.006 mole) in 300 ml of glacial acetic acid and under an atmosphere of hydrogen (44 psi) was shaken on a Parr apparatus at 85° for 4 days. The reaction mixture was filtered, and the solvent was removed in vacuo from the filtrate. The residue was partitioned between methylene chloride and dilute sodium hydroxide. The methylene chloride solution was dried over magnesium sulfate, and the solvent was removed in vacuo to give a solid. This was dissolved in a mixture of methanol-acetonitrile, and excess ethereal hydrogen chloride was added. A precipitate was collected to give 59.13 g (80.3%) of slightly impure title compound as a white, crystalline solid, mp 273°-274° C. Part of this was recrystallized from methanol-ether to give an analytically pure sample, mp 275.5°-277° C.

Analysis: Calculated for $C_{18}H_{22}ClN$: C, 75.11; H, 7.70; N, 4.87. Found: C, 75.03; H, 7.73; N, 4.93.

PREPARATION 40

α-(4-Fluorophenyl)-α-phenyl-4-pyridinemethanol

To a suspension of 18.5 g (0.761 mole) of magnesium turnings and several crystals of iodine in 800 ml of anhydrous ether, cooled in an ice bath and under an atmosphere of argon, was slowly added a solution of p-bromofluorobenzene in 200 ml of ether. The solution was stirred for 2 hr at 25° C. and 97.02 g (0.530 mole) of 4-benzoylpyridine was added as a solid. An additional 1 liter of anhydrous ether was added, and the solution was stirred at 25° C. for 3 hr. The reaction mixture was poured into an icy, aqueous solution of ammonium chloride. The mixture stood in the hood overnight and a white solid was collected. The solid was dissolved in a mixture of methanol-methylene chloride. The solution was filtered and the solvent was removed in vacuo. The residue was crystallized from chloroform-hexane to give 66.68 g (45%) of title compound as a white, crystalline solid, mp 189°-192° C. Part of this was recrystallized from methylene chloride-acetonitrile-hexane, mp 190°-192° C.

Analysis: Calculated for $C_{18}H_{14}FNO$: C, 77.40; H, 5.05; N, 5.02. Found: C, 77.24; H, 5.03; N, 4.9.

PREPARATION 41

α,α-Bis(4-fluorophenyl)-4-pyridineethanol

A solution of 27.8 g (0.30 mole) of 4-picoline in 400 ml of tetrahydrofuran and under an atmosphere of nitrogen was cooled to −30° C. in a dry-ice acetone bath.

A solution of 2.5 moles n-butyllithium in hexane (119 ml, 0.3 mole) was added over 1 hr and the mixture was stirred for an additional 30 min at −30° C. The reaction mixture was allowed to warm to room temperature over 1.5 hr, and 66.7 g (0.30 mole) of 4,4'-difluorobenzophenone in 100 ml of tetrahydrofuran was added. The mixture was stirred for 2 hr and then was poured into an icy solution of ammonium chloride. A white solid was collected. The aqueous mixture was extracted with several portions of methylene chloride and the methylene chloride then removed in vacuo to give additional solid. The solid fractions were combined and recrystallized from a mixture of ether-hexane to give 63.14 g (68% yield) of title compound as a white, crystalline solid, mp 158°–159.5° C.

Analysis: Calculated for $C_{19}H_{15}F_2NO$: C, 73.30; H, 4.86; N, 4.5. Found: C, 73.27; H, 4.79; N, 4.51.

PREPARATION 42

α,α-Bis(4-fluorophenyl)-4-piperidineethanol

A mixture of 12.25 g (0.0394 mole) of α,α-bis(4-fluorophenyl)-4-pyridineethanol and 1.3 g of 5% platinum on carbon catalyst in 250 ml of acetic acid was shaken under an atmosphere of hydrogen (53 psi) for 9 hr. The solution was filtered through Celite ®, and the solvent was removed in vacuo. The residue was partitioned between methylene chloride and dilute sodium hydroxide. The solvent was removed in vacuo to give a solid. Recrystallization from acetonitrile gave 10.62 g (85% yield) of title compound as a white, crystalline solid, mp 169°–171° C.

Analysis: Calculated for $C_{19}H_{21}F_2NO$: C, 71.90; H, 6.67; N, 4.41. Found: C, 71.98; H, 6.75; N, 4.54.

PREPARATION 43

4-[2,2-Bis(4-fluorophenyl)ethyl]pyridine hydrochloride [1:1]

A mixture of 15.05 g (0.048 mole) of α,α-bis(4-fluorophenyl)-4-pyridineethanol, 3.2 g (0.1 mole) of phosphorus and 50 ml of 56.9% hydrogen iodide in 150 ml of glacial acetic acid was heated at reflux for 11 hr. The solvent was removed in vacuo, and the residue was partitioned between methylene chloride and dilute sodium hydroxide. The methylene chloride solution was dried over magnesium sulfate, and the solvent was removed in vacuo to give an oil. This was dissolved in a mixture of methanol and ether, and an excess of ethereal hydrogen chloride was added. The solvent was removed in vacuo, and the residue was recrystallized from a mixture of acetonitrile and ether to give 13.89 g (87% yield) of title compound as a white, crystalline solid, mp 197°–199° C.

Analysis: Calculated for $C_{19}H_{16}ClF_2N$: C, 68.78; H, 4.86; N, 4.22. Found: C, 68.58; H, 5.17; N, 4.23.

PREPARATION 44

4-[2,2-Bis(4-fluorophenyl)ethyl]piperidine hydrochloride hydrate [1:1:0.5]

A mixture of 10.0 g (0.3 mole) α,α-bis(4-fluoropheny)-4-pyridineethanol and 1.2 g of 5% platinum on carbon catalyst in 200 ml of acetic acid was shaken under an atmosphere of hydrogen (49 psi) for 16 hr. The solution was filtered through Celite ®, and the solvent was removed in vacuo. The residue was partitioned between methylene chloride and dilute sodium hydroxide. The solvent was removed in vacuo to give an oil. This was dissolved in methanol, an excess of ethereal hydrogen chloride was added and ether was added. A precipitate was collected to give 7.58 g (72%) as a white crystalline solid, mp 171°–173° C.

Analysis: Calculated for $C_{19}H_{22}F_2N \cdot HCl \cdot 0.5H_2O$: C, 65.80; H, 6.68; N, 4.04. Found: C, 65.79; H, 6.80; N, 4.05.

PREPARATION 45

4-[2,2-Bis(4-fluorophenyl)ethylene]piperidine oxalate [1:1]

A mixture of 8.44 g (0.0266 mole) of α,α-bis(4-fluorophenyl)-4-piperidineethanol and 25 ml of concentrated sulfuric acid in 200 ml of glacial acetic acid was heated at reflux for 4 hr. The solvent was removed in vacuo, and the residue was made basic with 50% sodium hydroxide. The basic mixture was extracted with methylene chloride, and the methylene chloride solution was dried over magnesium sulfate. The solvent was removed in vacuo to give an oil. The oil was dissolved in a mixture of methanol/ether, and a slight excess of oxalic acid was added. Ether was added, and a precipitate was collected to give 8.79 g (85%) of title compound as a white, crystalline solid, mp 225°–225.5° C. with decomposition.

Analysis: Calculated for $C_{21}H_{21}F_2NO_4$: C, 64.78; H, 5.44; N, 3.6. Found: C, 64.95; H, 5.56; N, 3.61.

PREPARATION 46

1-Acetyl-4-(p-fluorobenzoyl)piperidine

A mixture of 93 g (0.7 mole) of aluminum chloride in 150 ml of fluorobenzene was stirred while 70 g (0.37 mole) of 1-acetylisonipecotic acid chloride was added in small portions. After the addition was complete, the mixture was heated at reflux for one hour. The mixture was poured onto ice, and the two resulting layers were separated. The aqueous layer was extracted twice with chloroform and the chloroform extracts were added to the fluorobenzene which was separated previously. The organic solution was dried over anhydrous sodium sulfate and filtered. The filtrate was concentrated, and 73.7 g (80%) of 1-acetyl-4-(p-fluorobenzoyl)piperidine was obtained as a crystalline residue. Recrystallization from ligroin-isopropyl ether gave a white, crystalline product melting at 75°–78° C.

Analysis: Calculated for $C_{14}H_{16}FNO_2$: C, 67.45; H, 6.47; N, 5.62. Found: C, 67.26; H, 6.50; N, 5.54.

PREPARATION 47

α-(4-Fluorophenyl)-α-(4-piperidinyl)-2-pyridinemethanol

To a stirred solution of 36.3 g (0.23 mole) of 2-bromopyridine in 500 ml of anhydrous tetrahydrofuran (THF) at −65° C. was added 88 ml (0.22 mole) of a commercial solution of 2.5M n-butyllithium in hexane at such a rate that the temperature did not exceed −60° C. The dark solution was stirred at −65° C. for 1 hr and then treated dropwise with a solution of 24.9 g (0.1 mole) of 1-acetyl-4-(p-fluorobenzoyl)piperidine in 250 ml of THF at such a rate that the temperature did not exceed −60° C. The mixture was stirred for 1 hr at −65° C. and overnight at ambient temperature. The dark mixture was poured into 2 liters of a saturated ammonium chloride solution. The layers were separated, and the aqueous layer was extracted once with a 500-ml portion of methylene chloride. The combined organic layers were washed successively with 500 ml of water, 500 ml of a 4% sodium hydroxide solution, 250 ml of water, and 250 ml brine.

All of the aqueous layers were combined and allowed to stand in a filter flask for several weeks. As the soluble organic solvents in the aqueous solution evaporated, a solid precipitated. The aqueous solution was decanted, and the solid was slurried with water, collected by filtration, and dried. The solid was recrystallized from absolute ethanol-pyridine to yield 4.5 g (14%) of the title compound as an off-white solid, mp 228°–230° C. (dec).

Analysis: Calculated for $C_{17}H_{19}FN_2O$: C, 71.31; H, 6.69; N, 9.78. Found: C, 71.43; H, 6.54; N, 9.52.

PREPARATION 48

Cyclohexyl[1-(phenylsulfonyl)-4-piperidinyl]methanone

To a solution of 25.1 g (0.085 mole) of 1-(phenylsulfonyl)-4-piperidinecarboxylic acid ethyl ester in 500 ml of dry tetrahydrofuran cooled to 0° C. and under an atmosphere of nitrogen, was added 95 ml of a 2 molar solution (0.19 mole) of cyclohexylmagnesium bromide in ether. The mixture was stirred for 2 hr at ambient temperature and then was quenched on an icy solution of ammonium chloride. The mixture was extracted with methylene chloride. The methylene chloride solution was dried over magnesium sulfate, and the solvent was removed in vacuo to give a semisolid material. This was recrystallized from ethanol to give 8.50 g (29.8% yield) of title compound as a white, crystalline solid, mp 141°–143° C.

Analysis: Calculated for $C_{18}H_{25}NO_3S$: C, 64.45; H, 7.51; N, 4.18. Found: C, 64.39; H, 7.82; N, 4.20.

PREPARATION 49

α-Cyclohexyl-α-(4-fluorophenyl)-1-(phenylsulfonyl)-4-piperidinemethanol

A solution of (4-fluorophenyl)[1-(phenylsulfonyl)-4-piperidinyl]methanone (20.8 g, 0.06 mole) in 250 ml of tetrahydrofuran (dried over 4A sieves) was prepared. This solution was stirred 0.5 hr under nitrogen in an ice bath. Next, cyclohexylmagnesium chloride (35 ml of 2M in diethyl ether, 0.07 mole) was added dropwise via syringe (under nitrogen). The resulting solution was stirred for 48 hr allowing the reaction solution to obtain room temperature. The reaction was concentrated to dryness and treated with aqueous ammonium chloride. The aqueous solution was extracted with chloroform, and the chloroform layer was washed with water. The chloroform layer was dried (anhydrous sodium sulfate) and filtered, and solvent removed to give a fluffy white residue. This material was subjected to flash chromatography on silica gel using 20% ethyl acetate-80% hexanes, and 30% ethyl acetate-70% hexanes for elution. Fractions containing a single spot were combined, and solvent was removed in vacuo. A fluffy, white residue was obtained and dried in vacuo overnight at 80° C. in the presence of phosphorus pentoxide. This procedure produced 16.72 g (64.7% yield) of white, crystalline solid, mp 106°–109° C.

Analysis: Calculated for $C_{24}H_{30}FNO_3S$: C, 66.79; H, 7.01; N, 3.24. Found: C, 66.78; H, 7.09; N, 3.21.

PREPARATION 50

4-[(Cyclohexyl)(4-fluorophenyl)methyl]pyridine

A mixture of α-cyclohexyl-α-(4-fluorophenyl)-4-pyridinemethanol (16.54 g, 0.058 mole), 57% hydrogen iodide (250 ml), glacial acetic acid (250 ml), and phosphorus (50.0 g) was heated overnight at reflux. The reaction mixture was cooled and filtered through Celite ®. The volume of the filtrate was concentrated to 100 ml. Ice/50% sodium hydroxide was added, and the aqueous phase was extracted with chloroform. The chloroform layer was back extracted with 5% sodium hydroxide and water. The organic layer was dried over sodium sulfate and filtered, and solvent removed to give a green oil. A 4 g portion of this oil was subjected to flash chromatography on silica gel using 20% ethyl acetate-hexanes for elution. Fractions of similar purity were combined and solvent removed to give an oil. This oil was dried in vacuo overnight at 80° C. The oil crystallized to give 2.95 g (19% yield) of white, crystalline solid, mp 78°–81° C.

Analysis: Calculated for $C_{18}H_{20}FN$: C, 80.26; H, 7.48; N, 5.2. Found: C, 79.96; H, 7.45; N, 5.23.

PREPARATION 51

4-[(Cyclohexyl)(4-fluorophenyl)methyl]piperidine

A mixture of 4-[(cyclohexyl)(4-fluorophenyl)methyl]pyridine (10.42 g, 0.039 mole), platinum oxide (1.5 g), and 10 drops of concentrated hydrochloric acid in 200 ml of glacial acetic was subjected to hydrogenation at 80° C. and 300 psi overnight, after which NMR analysis showed 50% desired product and 50% starting material. The reaction was repeated using 5% platinum on carbon at 85° C. and 1400 psi overnight. The reaction mixture was then cooled to room temperature and filtered. Solvent was removed by rotary evaporator. The oil obtained was dissolved in chloroform, and the solution was extracted with 5% sodium hydroxide and water. The chloroform layer was dried over sodium sulfate and filtered, and the solvent removed to give 9.94 g of brown oil. NMR analysis showed a 75%–25% mixture of product and starting material. The 9.94 g of oil obtained was dissolved in methanol and subjected to flash chromatography on silica gel using methanol and ammonium hydroxide-methanol for elution. Fractions of similar purity were combined and solvent removed. The clear oil obtained was dried in vacuo overnight at 80° C., to give 5.86 g (60% yield) of title compound as a clear oil.

Analysis: Calculated for $C_{18}H_{26}FN$: C, 78.50; H, 9.32; N, 5.09. Found: C, 78.26; H, 9.41; N, 5.06.

PREPARATION 52

4-(3-Chloropropoxy)-α-hydroxy-3-methoxybenzeneacetic acid (phenylmethyl) ester

A mixture of 2.92 g (0.008 mole) of 4-hydroxy-3-methoxymandelic acid (phenylmethyl) ester, 2 ml (0.02 mole) of 1-bromo-3-chloropropane, and 2.80 g (0.02 mole) of potassium carbonate in 40 ml of acetone was heated at reflux for 16 hours under nitrogen atmosphere during which time the solution changed from colorless to light-yellow. TLC (silica gel, hexanes/acetone 4:1) showed that the mandelate derivative had reacted, but 30–40% of unknown impurities had formed. The inorganic materials were separated by filtration, washed with acetone, and the filtrate was concentrated in vacuo at 60° C. to give 3.65 g of crude product. The material was purified by column chromatography (diameter 25 mm, using 80 g of silica gel) eluted with cyclohexane/ethyl acetate (6:1). The fractions containing the product were collected and the solid recrystallized from ethyl ether/hexanes to give 0.637 g (22%) of material as a white powder.

PREPARATION 53

4-[3-[4-[Bis(4-Fluorophenyl)hydroxymethyl]-1-piperidinyl]-propoxy]-α-hydroxy-3-methoxybenzeneacetic acid (phenylmethyl) ester A mixture of 0.637 g (0.00175 mole) 4-(3-chloropropoxy)-3-methoxymandelic acid phenylmethyl ester, 0.545 g (0.00180 mole) of [α,α-bis(4-fluorophenyl)]-4-piperidinemethanol hydrochloride, and 0.3 ml (0.0025 mole) of triethylamine in 3 ml of benzyl alcohol was heated under nitrogen atmosphere at 110° C. for 7 hours while the reaction was monitored by TLC (silica gel, methylene chloride/methanol/ammonium hydroxide 90:10:1). The reaction mixture was concentrated in vacuo, ethyl ether (60 ml) and hexanes (40 ml) were added to the oily residue, and the solution was kept in the refrigerator for 2 hours. The solid that formed was filtered, washed with ether and dissolved in methylene chloride (40 ml). The methylene chloride solution was washed with water ($3 \times 10$ ml) and dried (sodium sulfate), and the solvent was evaporated in vacuo to give 0.6 g of an oil. Final purification was done using 6 tapered silica gel plates $20 \times 20$ cm eluting with methylene chloride/methanol/ammonium hydroxide (90:5:0.5). The TLC sections containing the product were scraped off, and eluted with the above solvent system to give 0.4 g (34%) of the product as a light-amber oil. $^1$H NMR and mass spectral analysis support the structure assigned.

PREPARATION 54

4,α-Dihydroxy-3-methoxybenzeneacetic acid, (phenylmethyl) ester

To a mixture of 4.371 g (0.022 mole) of 4-hydroxy-3-methoxymandelic acid, 11 ml of triethylamine in 100 ml of acetone was added 3.13 ml (0.0265 mole) of benzyl bromide. The reaction mixture was stirred (magnetic stirring) and heated at reflux (oil bath) under a nitrogen atmosphere. After 5 minutes of heating the reaction mixture became cloudy. Thin layer chromatography (TLC) (silica gel, acetone/ethyl acetate 95:5) showed 50% of the starting material remaining after 5 hours. Additional triethylamine (2 ml) and benzyl bromide (1.5 ml) were added, and the mixture was heated at reflux for 4 hours. TLC still showed starting material present. Additional reagents were added (1.5 ml benzyl bromide and 2 ml triethylamine) and heating was continued for 14 hours. The triethylamine hydrobromide was removed by filtration, and the filter cake was washed with acetone ($3 \times 10$ ml). The filtrate and washings were evaporated to give 17.6 g of a semi-solid residue. The residue was triturated with water (30 ml), and the product extracted with methylene chloride ($4 \times 15$ ml) and dried (sodium sulfate). Evaporation of the solvent yielded 4.99 g of a light-brown oil which was triturated with hexanes (20 ml) to crystallize the product. The cream-colored solid was separated and washed with hexanes ($3 \times 10$ ml) to give 3.351 g (53% yield) of the product. Estimated purity by TLC was 98% (hexanes/acetone 5:1).

PREPARATION 55

α,α-Bis(4-fluorophenyl-4-piperidineacetamide monohydrochloride

A solution of α,α-bis(4-fluorophenyl)-4-piperidineacetonitrile (9.31 g, 0.0298 mol) in 100 ml of 90% sulfuric acid was heated overnight at 85° C. The solution was cooled to room temperature and made alkaline with 50% sodium hydroxide/ice. The aqueous layer was extracted with chloroform. The chloroform layer was dried (sodium sulfate) and filtered, and the solvent was removed in vacuo giving a white solid (9.19 g, 93.4%). A portion (2.25 g) of the white solid was converted to the HCl salt and the salt was recrystallized from 2-propanol-diethyl ether. This furnished a white solid which was dried in vacuo overnight at 80° C. This process provided 0.54 g of white crystalline solid, mp 328° C. (dec).

Analysis: Calculated for $C_{19}H_{20}F_2N_2O \cdot HCl$: C, 62.21; H, 5.77; N, 7.64. Found: C, 61.81; H, 5.89; N, 7.45.

PREPARATION 56

4-[2-Amino-1,1-bis(4-fluorophenyl)-2-oxoethyl]-1-piperidinecarboxylic acid methyl ester A mixture of α,α-bis(4-fluorophenyl)-4-piperidineacetamide (7.65 g, 0.023 mol) and sodium bicarbonate (3.36 g, 0.023 mole) in methylene chloride was prepared. To this mixture was added a solution of methyl chloroformate (2.17 g, 0.023 mole) in methylene chloride. The resulting mixture was stirred overnight at room temperature. The mixture was extracted successively with water, 5% sodium hydroxide, and water. The methylene chloride layer was dried (sodium sulfate). The organic layer was filtered, and solvent was removed to provide a fluffy, white residue (5.95 g, 66.6% yield). A 0.5 g sample was crystallized from methylene chloridehexanes. This provided a white solid which was dried in vacuo overnight at 80° C., mp 126°–129° C.

Analysis: Calculated for $C_{21}H_{22}F_2N_2O_3$: C, 64.94; H, 5.71; N, 7.21. Found: C, 64.83; H, 5.97; N, 6.92.

PREPARATION 57

4[α,α-Bis(4-fluorophenyl)][(methoxycarbonyl)amino]-methyl]-1-piperidinecarboxylic acid methyl ester A solution of 4-[2-amino-1,1-bis(4-fluorophenyl)-2-oxoethyl]-1-piperidinecarboxylic acid methyl ester (3.88 g, 0.01 mol) and 50% sodium hydroxide (4.0 g, 0.05 mol) in 40 ml of methanol was prepared. To this solution was added dropwise a solution of bromine (4.04 g, 0.025 mol) in 25 ml of methanol. The resulting solution was stirred for 0.5 h at room temperature and then heated at reflux for 16 h. The reaction was concentrated to dryness, and the residue obtained was partitioned between chloroform and water. The chloroform layer was dried (sodium sulfate) filtered, and solvent removed to give a fluffy white residue (3.60 g, 86.1%). A small sample (0.26 g) was subjected to flash chromatography on a ten-gram silica gel column using 50% ethyl acetate-50% hexanes for elution. A white solid was isolated and dried in vacuo overnight at 80° C. This provided 0.13 g (43% based on aliquot taken) of white, crystalline solid, mp 213° C.

Analysis: Calculated for $C_{22}H_{24}F_2N_2O_4$: C, 63.15; H, 5.78; N, 6.7. Found: C, 62.64; H, 5.81; N, 6.53.

PREPARATION 58

α,α-Bis(4-fluorophenyl)-4-piperidinemthanamine oxalate hydrate (2:4:1)

A mixture of 4-[α,α-bis(4-fluorophenyl)[(methoxycarbonyl)amino]methyl]-1-piperidinecarboxylic acid methyl ester (2.98 g, 0.00713 mole), and 50% sodium hydroxide (20 g, 0.25 mole) in 40 ml of methanol was subject to reflux for 16 hours. The mixture was cooled to room temperature and concentrated on a rotary evaporator. Water was added to the residue, and the mixture was extracted with chloroform. The chloroform extract was washed with water, dried over sodium sulfate and filtered. The chloroform was removed to give 1.9 g (88.2%) of yellow oil. This oil was converted to the fumarate, but an analytically pure sample could not be obtained. The fumarate was converted back to the free base and the base was converted to an oxalate. The salt was recrystallized from methanol and diethyl ether. The oxalate was then dissolved in methanol and filtered. Methanol was removed to give a light yellow solid which was dried 16 hours in vacuo at 80° C. This furnished 0.25 g (7.1%) of white, crystalline solid mp 151°–154° C.

Analysis: Calc. for $C_{18}H_{20}F_2N_2.2C_2H_2O_4.0.5H_2O$: C, 53.77; H, 5.13; N, 5.7. Found: C, 53.39; H, 5.20; N, 6.04.

EXAMPLE 1

4-[3-[4-[Bis(4-fluorophenyl)hydroxymethyl]-1-piperidinyl]propoxy-3-methoxy-α-oxobenzeneacetic acid A mixture of 0.02 mole of [α,α-bis(4-fluorophenyl)]-4-piperidinemethanol, 0.02 mole of 4-(3-chloropropyloxy)-3-methoxy-α-oxobenzeneacetic acid ethyl ester, 0.06 mole of anhydrous sodium carbonate and 0.4 g of potassium iodide in 150 ml of dimethylformamide was heated on a steambath overnight. The mixture was poured into 1.5 liters of ice-water, and the ethyl ester of the title compound precipitated. The liquid was decanted, and the gum was dissolved in 100 ml of ethanol. A solution of 0.04 mole of sodium bicarbonate in 20 ml of water was added, and the mixture was heated at reflux overnight and then poured into a solution of 1 liter of water and 5 ml of acetic acid. Sodium chloride was added, and a solid precipitated. The solid was collected by filtration and dried to give the title compound.

EXAMPLE 2

4-[3-[4-[Bis(4-fluorophenyl)hydroxymethyl]-1-piperidinyl]propoxy]-α-hydroxy-3-methoxybenzeneacetic acid hemihydrate A mixture of 0.40 g (0.00063 mole) of 4-[3-[4-[bis(4-fluorophenyl)hydroxymethyl]-1-piperidinyl]propoxy-α-hydroxy]-3-methoxybenzeneacetic acid (phenylmethyl) ester, 0.044 g of 5% palladium on carbon, 3.5 ml of acetic acid and 35 ml of absolute ethanol was hydrogenated in a Parr apparatus at 45 psi at ambient temperature while the progress of the reaction was monitored by TLC (silica gel, methylene chloride/methanol/ammonium hydroxide 70:30:1). The catalyst was separated by filtration and washed with acetonitrile. The filtrate was evaporated in vacuo at ambient temperature, and the residue was triturated with ethyl ether and methanol. The white solid was collected by filtration and vacuum dried at 60° C. to give 0.235 g (72% yield) of the title compound, mp 153°–155° C. (sealed tube).

Analysis: Calculated for $C_{30}H_{33}F_2NO_6.0.5H_2O$: C, 65.44; H, 6.22, N, 2.54. Found: C, 65.76; H, 6.10; N, 2.57.

EXAMPLE 3

α,α-Bis(4-fluorophenyl)-1-[3-[4-(2-hydroxyethyl)-2-methoxyphenoxy]propyl]-4-piperidinemethanol.oxalate.2-propanol (1:1.5:1)

To a stirred slurry of 0.5 g (0.013 mole) of lithium aluminum hydride in 50 ml of dry tetrahydrofuran was added dropwise a solution of 6.1 g (0.011 mole) of 4-[3-[4-[bis(4-fluorophenyl)hydroxymethyl]-1-piperidinyl]-propoxy]-3-methoxybenzene acetic acid ethyl ester (Preparation 17) in 100 ml of dry tetrahydrofuran. The mixture was stirred at ambient temperature overnight, and the excess lithium aluminum hydride decomposed by successive additions of 0.5 ml of water, 0.5 ml of a 20% sodium hydroxide solution and 1.5 ml of water. The mixture was stirred for 2 hr and filtered. The filtrate was concentrated to give a gum, which was converted to the oxalic acid salt in 2-propanol to yield 4.7 g of the title compound as a white solid, mp 78°–92° C. (decomposes).

Analysis: Calc. for $C_{30}H_{35}F_2NO_4.1.5C_2H_2O_4.C_3H_8O$: C, 61.18; H, 6.56; N, 1.98. Found: C, 61.17; H, 6.56; N, 2.

EXAMPLE 4

α,α-Bis(4-fluorophenyl)-1-[3-[4-(2-hydroxymethyl)-2-methoxyphenoxy]propyl]-4-piperidinemethanol oxalate hydrate compound with 2-propanol [1:1.5:0.5:1]

To a slurry of 0.6 g (0.015 mol) of lithium aluminum hydride (LAH) in 50 ml of dry tetrahydrofuran (THF) was added dropwise a solution of 5.3 g (0.01 mol) of 4-[3-[4-[bis(4-fluorophenyl)hydroxymethyl]-1-piperidinyl]propoxy]-3-methoxybenzoic acid methyl ester in 100 mL of dry THF. The mixture was stirred at ambient temperature overnight and then the excess LAH was decomposed with successive additions of 0.5 ml of water, 0.5 mL of a 20% sodium hydroxide solution and 1.5 mL of water. The mixture was stirred for 1 h and then filtered. The filtrate was concentrated to give a gum as residue. The gum was converted to the oxalic acid salt, and the solid was recrystallized from 2-propanol to give 4.8 g (69%) yield of title compound as a white solid, mp 72°–77° C.

Analysis: Calc for $C_{29}H_{33}F_2NO_4.1.5C_2H_4O_4.0.5H_2O.C_3H_8O$: C, 59.90; H, 6.46; H, 6.46; N, 2. Found: C, 59.55; H, 6.29; N,2.05.

EXAMPLE 5

1-[4-[3-[4-[Bis(4-fluorophenyl)hydroxymethyl]-1-piperidinyl]propoxy]-3-methoxyphenyl]-2-hydroxyethanone.

A solution of 3.9 g (0.0069 mole) of 2-(acetyloxy)-1-[4-[3-[4-[bis(4-fluorophenyl)hydroxymethyl]-1-piperidinyl]propoxy]-3-methoxyphenyl]ethanone and 1.2 g (0.02 mole) of potassium hydroxide in 50 ml of 95% ethanol and 10 ml of water was heated at reflux under a nitrogen atmosphere for 4 hr. The solution was poured into 600 ml of ice-water and sodium chloride was added until a solid precipitated. The solid was collected by filtration and dried under vacuum to give the title compound. The compound is air sensitive and must be handled in an inert atmosphere.

EXAMPLE 6

1-[4-[3-[4-Bis(4-fluorophenyl)hydroxymethyl]-1-piperidinyl]propoxy]-3-methoxyphenyl]-1,2-ethanediol A mixture of 0.02 mole of 2-(acetyloxy)-1-[4-[3-[4-[bis(4-fluorophenyl)hydroxymethyl]-1-piperidinyl]-propoxy]-3-methoxyphenyl]ethanone and 0.11 mole of sodium borohydride in 100 ml of t-butyl alcohol was heated at reflux and treated dropwise with 16 ml of methanol over a 1 hr period. The mixture was heated at reflux for an additional 1 hr and cooled, and water was then added to quench the reaction. The mixture was concentrated and the residue was partitioned between methylene chloride and water. The organic layer was dried over sodium sulfate and concentrated to give the title compound.

EXAMPLE 7

When in the procedure of Example 1 and substituting the following for [α,α-bis(4-fluorophenyl)]-4-piperidinemethanol:
a. 4-[(3,4-difluorophenyl)(4-fluorophenyl)methylene]-piperidine,
b. 4-[(3,4-difluorophenyl)(4-fluorophenyl)methyl]-piperidine,
c. 4-[bis(2,4-difluorophenyl)methyl]piperidine,
d. α,α-bis(3-fluorophenyl)-4-piperidinemethanol,
e. α,α-bis(4-fluorophenyl)-4-piperidineacetonitrile, and
f. α,α-bis(4-fluorophenyl)-3-pyrrolidineacetonitrile
there are obtained:
a. 4-[3-[4-[(3,4-difluorophenyl)(4-fluorophenyl)methylene]-1-piperidinyl]propoxy]-3-methoxy-α-oxobenzeneacetic acid,
b. 4-[3-[4-[(3,4-difluorophenyl)(4-fluorophenyl)methyl]-1-piperidinyl]propoxy]-3-methoxy-α-oxobenzeneacetic acid,
c. 4-[3-[4-[bis(2,4-difluorophenyl)methyl]-1-piperidinyl]propoxy]-3-methoxy-α-oxo-benzeneacetic acid,
d. 4-[3-[4-bis(3-fluorophenyl)hydroxymethyl-1-piperidinyl]propoxy]-3-methoxy-α-oxobenzeneacetic acid,
e. 4-[3-[4-[α,α-bis(4-fluorophenyl)cyanomethyl]-1-piperidinyl]propoxy]-3-methoxy-α-oxobenzeneacetic acid, and
f. 4-[3-[3-[α,α-bis(4-fluorophenyl)cyanomethyl]-1-pyrrolidinyl]propoxy]-3-methoxy-α-oxobenzeneacetic acid.

EXAMPLE 8

When in the procedure of Example 2 and substituting the following for 4-[3-[4-[bis(4-fluorophenyl)hydroxymethyl]-1-piperidinyl]propoxy]-3-methoxy-α-oxobenzeneacetic acid ethyl ester;
a. 4-[3-[4-[(3,4-difluorophenyl)(4-fluorophenyl)methylene]-1-piperidinyl]propoxy]-3-methoxy-α-oxobenzene acetic acid ethyl ester,
b. 4-[3-[4-[(3,4-difluorophenyl)(4-fluorophenyl)methyl]-1-piperidinyl]propoxy]-3-methoxy-α-oxobenzene acetic acid ethyl ester,
c. 4-[3-[4-[bis(2,4-difluorophenyl)methyl]-1-piperidinyl]propoxy]-3-methoxy-α-oxobenzeneacetic acid ethyl ester,
d. 4-[3-[4-[bis(3-difluorophenyl)hydroxymethyl]-1-piperidinyl]propoxy]-3-methoxy-α-oxobenzeneacetic acid ethyl ester,
e. 4-[3-[4-[α,α-bis(4-fluorophenyl)cyanomethyl]-1-piperidinyl]propoxy]-3-methoxy-α-oxobenzeneacetic acid ethyl ester, and
f. 4-[3-[3-[bis(3-fluorophenyl)cyanomethyl]-1-piperidinyl]propoxy]-3-methoxybenzeneacetic acid ethyl ester
there are obtained:
a. 4-[3-[4-[(3,4-difluorophenyl)(4-fluorophenyl)methylene]-1-piperidinyl]propoxy]-α-hydroxy-3-methoxybenzeneacetic acid,
b. 4-[3-[4-[(3,4-difluorophenyl)(4-fluorophenyl)methyl]-1-piperidinyl]propoxy]-α-hydroxy-3-methoxyoxobenzene acetic acid,
c. 4-[3-[4-[bis(2,4-difluorophenyl)methyl]-1-piperidinyl]propoxy]-α-hydroxy-3-methoxybenzeneacetic acid,
d. 4-[3-[4-[bis(3-fluorophenyl)hydroxymethyl]-1-piperidinyl]propoxy]-α-hydroxy-3-methoxybenzeneacetic acid,
e. 4-[3-[4-[bis(4-fluorophenyl)cyanomethyl]-1-piperidinyl]propoxy]-α-hydroxy-3-methoxybenzeneacetic acid, and
f. 4-[3-[3-[bis(4-fluorophenyl)cyanomethyl]-1-piperidinyl]propoxy]-α-hydroxy-3-methoxybenzeneacetic acid.

EXAMPLE 9

When in the procedure of Example 3, and substituting the following for 4-[3-[4-[bis(4-fluorophenyl)hydroxymethyl]-1-piperidinyl]propoxy]-3-methoxybenzeneacetic acid ethyl ester:
a. 4-[3-[4-[(3,4-difluorophenyl)(4-fluorophenyl)methylene]-1-piperidinyl]propoxy]-3-methoxybenzeneacetic acid ethyl ester,
b. 4-[3-[4-[(3,4-difluorophenyl)(4-fluorophenyl)methyl]-1-piperidinyl]propoxy]-3-methoxybenzeneacetic acid ethyl ester,
c. 4-[3-[4-[bis(2,4-difluorophenyl)methyl]-1-piperidinyl]propoxy]-3-methoxybenzeneacetic acid ethyl ester,
d. 4-[3-[4-[bis(3-fluorophenyl)hydroxymethyl]-1-piperidinyl]propoxy]-3-methoxybenzeneacetic acid ethyl ester,
e. 4-[3-[4-[bis(4-fluorophenyl)cyanomethyl]-1-piperidinyl]propoxy]-3-methoxybenzeneacetic acid ethyl ester, and
f. 4-[3-[3-[bis(4-fluorophenyl)cyanomethyl]-1-pyrrolidinyl]propoxy]-3-methoxybenzeneacetic acid ethyl ester.
there are obtained:
a. 2-[4-[3-[4-[(3,4-difluorophenyl)(4-fluorophenyl)methylene]-1-piperidinyl]propoxy]-3-methoxyphenyl]ethanol,
b. 2-[4-[3-[4-[(3,4-difluorophenyl)(4-fluorophenyl)methyl]-1-piperidinyl]propoxy]-3-methoxyphenyl]ethanol,
c. 2-[4-[3-[4-[bis(2,4-difluorophenyl)methyl]-1-piperidinyl]propoxy]-3-methoxyphenyl]ethanol,
d. α,α-bis(3-fluorophenyl)-1-[3-[4-(2-hydroxyethyl)-2-methoxyphenoxy]propyl]-4-piperidinemethanol,
e. α,α-bis(4-fluorophenyl)-1-[3-[4-(2-hydroxyethyl)-2-methoxyphenoxy]propyl]-4-piperidineacetonitrile, and
f. α,α-bis(4-fluorophenyl)-1-[3-[4-(2-hydroxyethyl)-2-methoxyphenoxypropyl]-3-pyrrolidineacetonitrile.

EXAMPLE 10

When in the procedure of Example 4, and substituting the following for 4-[3-[4-[bis(4-fluorophenyl)hydroxymethyl]-1-piperidinyl]propoxy]-3-methoxybenzoic acid methyl ester:

a. 4-[3-[4-[(3,4-difluorophenyl)(4-fluorophenyl)methylene]-1-piperidinyl]propoxy]-3-methoxybenzoic acid methyl ester,
b. 4-[3-[4-[(3,4-difluorophenyl)(4-fluorophenyl)methyl]-1-piperidinyl]propoxy]-3-methoxybenzoic acid methyl ester,
c. 4-[3-[4-[bis(2,4-difluorophenyl)methyl]-1-piperidinyl]propoxy]-3-methoxybenzoic acid methyl ester,
d. 4-[3-[4-[bis(3-fluorophenyl)hydroxymethyl]-1-piperidinyl]propoxy]-3-methoxybenzoic acid methyl ester,
e. 4-[3-[4-[bis(4-fluorophenyl)cyanomethyl]-1-piperidinyl]propoxy]-3-methoxybenzoic acid methyl ester,
f. 4-[3-[3-[bis(4-fluorophenyl)cyanomethyl]-1-pyrrolidinyl]propoxy]-3-methoxybenzoic acid methyl ester, there are obtained:

a. 4-[3-[4-[(3,4-difluorophenyl)(4-fluorophenyl)methylene]-1-piperidinyl]propoxy]-3-methoxyphenyl]methanol,
b. 4-[3-[4-[(3,4-difluorophenyl)(4-fluorophenyl)methyl]-1-piperidinyl]propoxy]-3-methoxyphenylmethanol,
c. 4-[3-[4-[bis(2,4-difluorophenyl)methyl]-1-piperidinyl]propoxy]-3-methoxyphenylmethanol,
d. α,α-bis(3-fluorophenyl)-1-[3-[4-(hydroxymethyl)-2-methoxyphenoxy]propyl]-4-piperidinemethanol,
e. α,α-bis(4-fluorophenyl)-1-[3-[4-(hydroxymethyl)-2-methoxyphenoxy]propyl]-4-piperidineacetonitrile, and
f. α,α-bis(4-fluorophenyl)-1-[3-[4-(hydroxymethyl)-2-methoxyphenoxy]propyl]-3-pyrrolidineacetonitrile.

EXAMPLE 11

When in the procedure of Example 5, and substituting the following for 2-(acetyloxy)-2-[4-[3-[4-[bis(4-fluorophenyl)hydroxymethyl]-1-piperidinyl]propoxy]-3-methoxyphenyl]ethanone:

a. 2-acetyloxy-1-[4-[3-[4-[(3,4-difluorophenyl)(4-fluorophenyl)methylene]-1-piperidinyl]propoxy]-3-methoxyphenyl]ethanone,
b. 2-acetyloxy-1-[4-[3-[4-[(3,4-difluorophenyl)(4-fluorophenyl)methyl]-1-piperidinyl]propoxy]-3-methoxyphenyl]ethanone,
c. 2-acetyloxy-1-[4-[3-[4-[bis(2,4-difluorophenyl)methyl]-1-piperidinyl]propoxy]-3-methoxyphenyl]ethanone,
d. 2-acetyloxy-1-[4-[3-[4-[bis(3-fluorophenyl)hydroxymethyl]-1-piperidinyl]propoxy]-3-methoxyphenyl]ethanone
e. 1-[3[4-(2-Acetoxy-1-oxoethyl)-2-methoxyphenoxy]propyl]-α,α-bis(4-fluorophenyl)-4-piperidineacetonitrile, and
f. 1-[3[4-(2-Acetoxy-1-oxoethyl)-2-methoxyphenoxy]propyl]-α,α-bis(4-fluorophenyl)-3-pyrrolidineacetonitrile.

there are obtained:

a. 1-[4-[3-[4-[(3,4-difluorophenyl)(4-fluorophenyl)methylene]-1-piperidinyl]propoxy]-3-methoxyphenyl]-2-hydroxyethanone,
b. 1-[4-[3-[4-(3,4-difluorophenyl)(4-fluorophenyl)methyl]-1-piperidinyl]propoxy]-3-methoxyphenyl]-2-hydroxyethanone,
c. 1-[4-[3-[4-[bis(2,4-difluorophenyl)methyl]-1-piperidinyl]propoxy]-3-methoxyphenyl]-2-hydroxyethanone,
d. 1-[4-[3-[4-[bis(3-fluorophenyl)hydroxymethyl]-1-piperidinyl]propoxy]-3-methoxyphenyl]-2-hydroxyethanone,
e. α,α-bis(4-fluorophenyl)-1-[3-[4-(hydroxyacetyl)-2-methoxyphenoxy]propyl]-4-piperidineacetonitrile,
f. α,α-bis(4-fluorophenyl)-1-[3-[4-(hydroxyacetyl)-2-methoxyphenoxy]propyl]-3-pyrrolidineacetonitrile.

EXAMPLE 12

When in the procedure of Example 6, and substituting the following for 2-(acetyloxy)-1-[4-[3-[4-[bis(4-fluorophenyl)hydroxymethyl]-1-piperidinyl]propoxy]-3-methoxyphenyl]ethanone:

a. 2-acetyloxy-1-[4-[3-[4-[(3,4-difluorophenyl)(4-fluorophenyl)methylene]-1-piperidinyl]propoxy]-3-methoxyphenyl]ethanone,
b. 2-acetyloxy-1-[4-[3-[4-[(3,4-difluorophenyl)(4-fluorophenyl)methyl]-1-piperidinyl]propoxy]-3-methoxyphenyl]ethanone,
c. 2-acetyloxy-1-[4-[3-[4-[bis(2,4-difluorophenyl)methyl]-1-piperidinyl]propoxy]-3-methoxyphenyl]ethanone,
d. 2-acetyloxy-1-[4-[3-[4-[bis(3-fluorophenyl)hydroxymethyl]-1-piperidinyl]propoxy]-3-methoxyphenyl]ethanone
e. α,α-bis(4-fluorophenyl)-1-[2-methoxy-4-[2-acetyloxy-1-ethanone]phenoxy]-4-piperidineacetonitrile, and
f. α,α-bis(4-fluorophenyl)-1-[2-methoxy-4-[2-acetyloxy-1-ethanone]phenoxy]-3-pyrrolidineacetonitrile.

there are obtained:

a. 1-[4-[3-[4-[(3,4-difluorophenyl)(4-fluorophenyl)methylene]-1-piperidinyl]propoxy]-3-methoxyphenyl]1,2-ethanediol,
b. 1-[4-[3-[4-[(3,4-difluorophenyl)(4-fluorophenyl)methyl]-1-piperidinyl]propoxy]-3-methoxyphenyl]-1,2-ethanediol,
c. 1-[4-[3-[4-[bis(2,4-difluorophenyl)methyl]-1-piperidinyl]propoxy]-3-methoxyphenyl]-1,2-ethanediol,
d. α,α-bis(3-fluorophenyl)-1-[3-[4-[1,2-dihydroxyethane]-2-methoxyphenoxy]propyl]-4-piperidinemethanol,
e. α,α-bis(4-fluorophenyl)-1-[3-[4-[1,2-dihydroxyethane]-2-methoxyphenoxy]propyl]-4-piperidineacetonitrile, and
f. α,α-bis(4-fluorophenyl)-1-[3-[4-[1,2-dihydroxyethane]-2-methoxyphenoxy]propyl]-3-pyrrolidineacetonitrile.

EXAMPLE 13

When in the procedure of example 1 and substituting the following for α,α-bis(4-fluorophenyl)-4-piperidinemethanol:

a. 4-diphenylmethylenepiperidine
b. 4-[bis(4-fluorophenylmethylene]piperidine,
c. 4-[bis(4-fluorophenyl)methyl]piperidine
d. 4-[α-(p-fluorophenyl)-α-phenyl]-4-piperidinemethanol,
e. α-(4-fluorophenyl)-α-phenyl-4-piperidinemethanol,
f. 4-(diphenylmethyl)piperidine,
g. α,α-bis(4-fluorophenyl)-4-piperidineethanol,
h. 4-[2,2-bis(4-fluorophenyl)ethyl]piperidine, and i. 4-[2,2-bis(4-fluorophenyl)ethylene]piperidine
there are obtained:
a. 4-[3-[4-(diphenylmethylene)-1-piperidinyl]propoxy]-3-methoxy-α-oxobenzeneacetic acid,
b. 4-[3-[4-[bis(4-fluorophenyl)methylene]-1-piperidinyl]propoxy]-3-methoxy-α-oxobenzeneacetic acid,
c. 4-[3-[4-[bis(4-fluorophenyl)methyl]-1-piperidinyl]propoxy]-3-methoxy-α-oxobenzeneacetic acid,
d. 4-[3-[4-[α-(4-fluorophenyl)-α-phenylmethyl]-1-piperidinyl]propoxy]-3-methoxy-α-oxobenzeneacetic acid,
e. 4-[3-[4-[α-(4-fluorophenyl)-α-phenylhydroxymethyl]-1-piperidinyl]propoxy]-3-methoxy-α-oxobenzeneacetic acid,
f. 4-[3-[4-(diphenylmethyl)-1-piperidinyl]propoxy]-3-methoxy-α-oxobenzeneacetic acid,
g. 4-[3-[4-[2,2-bis(4-fluorophenyl)-2-hydroxyethyl]-2-piperidinyl]propoxy]-3-methoxy-α-oxobenzeneacetic acid,
h. 4-[3-[4-[2,2-bis(4-fluorophenyl)ethyl]-1-piperidinyl]propoxy]-3-methoxy-α-oxobenzeneacetic acid, and
i. 4-[3-[4-[2,2-bis(4-fluorophenyl)ethylene]-1-piperidinyl]propoxy]-3-methoxy-α-oxobenzeneacetic acid.

EXAMPLE 14

When in the procedure of Example 1 and substituting the following for α,α-bis(4-fluorophenyl)-4-piperidinemethanol:
a. α-(4-fluorophenyl)-α-(4-piperidinyl)-2-pyridinemethanol, and
b. 4-[(cyclohexyl)(4-fluorophenyl)methyl]piperidine
there are obtained:
a. 4-[3-[4-[α-(4-fluorophenyl)-α-(2-pyridinyl)hydroxymethyl]-1-piperidinyl]propoxy]-3-methoxy-α-oxobenzeneacetic acid, and
b. 4-[3-[4-[(cyclohexyl)(4-fluorophenyl)methyl]-1-piperidinyl]propoxy]-3-methoxy-α-oxobenzeneacetic acid.

EXAMPLE 15

When in the procedure of Example 2, and substituting the following for 4-[3-[4-[bis(4-fluorophenyl)hydroxymethyl]-1-piperidinyl]propoxy]-3-methoxy-α-oxobenzeneacetic acid:
a. 4-[3-[4-[bis(4-fluorophenyl)methylene]-1-piperidinyl]propoxy]-3-methoxy-α-oxobenzeneacetic acid, and
b. 4-[3-[4-[bis(4-fluorophenyl)methyl]-1-piperidinyl]propoxy]-3-methoxy-α-oxobenzeneacetic acid.
there are obtained:
a. 4-[3-[4-[bis(4-fluorophenyl)methylene]-1-piperidinyl]propoxy]-α-hydroxy-3-methoxybenzeneacetic acid, and
b. 4-[3-[4-[bis(4-fluorophenyl)methyl]-1-piperidinyl]propoxy]-α-hydroxy-3-methoxybenzeneacetic acid.

EXAMPLE 16

2-(Acetyloxy)-1-[4-[3-[bis(4-fluorophenyl)hydroxymethyl]-1-piperidinyl]propoxy]-3-methoxyphenyl]ethanone A mixture of 9.1 g (0.03 mole) of α,α-bis(p-fluorophenyl)-4-piperidinemethanol and 9.0 g (0.03 mole) of 2-(acetyloxy)-1-[4-(3-chloropropoxy)-3-methoxyphenyl]ethanone, 10.6 g (0.1 mole) of anhydrous sodium carbonate and 0.6 g of potassium iodide in 200 ml of dimethylformamide was heated on a steambath for 20 hr. The mixture was concentrated under reduced pressure, and the residue was partitioned between water and benzene. The benzene layer was washed with water and saturated sodium chloride solution, dried over anhydrous sodium sulfate and concentrated under reduced pressure to give a solid residue. The solid was purified by column chromatography on 300 g of Florisil®. Fractions eluted with 2.5-3.5% acetone in benzene were combined and concentrated to give 11.8 g (69% yield) of title compound as pale-yellow crystals. The crystals were recrystallized from isopropyl ether-benzene, mp 138°-140° C.

Analysis: Calculated for $C_{32}H_{35}F_2NO_6$: C, 67.71; H, 6.22; N, 2.47. C, 67.97; H, 6.26; N, 2.47.

EXAMPLE 17

4-[3-[4-[Bis(4-fluorophenyl)hydroxymethyl]-1-piperidinyl]propoxy]-3-methoxybenzeneacetic acid ethyl ester A mixture of 9.1 g (0.03 mole) of [α,α-bis(p-fluorophenyl)]-4-piperidinemethanol and 8.6 g (0.03 mole) of 4-(3-chloropropoxy)-3-methoxybenzeneacetic acid ethyl ester, 10.6 g (0.1 mole) of anhydrous sodium carbonate and 0.5 g of potassium iode in 150 ml of dimethylformamide was heated on a steambath for 20 hr. The mixture was concentrated under reduced pressure and the residue was partitioned between water and benzene. The benzene layer was washed with water and saturated sodium chloride solution, dried over anhydrous sodium sulfate and concentrated under reduced pressure to give an off-white solid which was recrystallized from isopropyl ether/2-propanol. The yield of the title compound was 12.7 g (77%), mp 110°-112° C.

Analysis: Calculated for $C_{32}H_{37}F_2NO_5$: C, 69.42; H, 6.74; N, 2.53. Found: C, 69.36; H, 6.79; N, 2.52.

EXAMPLE 18

α,α-Bis(4-fluorophenyl)-1-[3-[4-(1-hydroxyethyl)-2-methoxyphenoxy]propyl]-4-piperidinemethanol oxalate (1:1) sesquihydrate To a stirred slurry of 0.6 g (0.015 mole) of lithium aluminum hydride in 50 ml of dry tetrahydrofuran (THF) was added a solution of 7.6 g (0.015 mole) of 1-[4-[3-[4-[bis(4-fluorophenyl)hydroxymethyl]-1-piperidinyl]propoxy]-3-methoxyphenyl]ethanone in 100 ml of dry THF. The mixture was stirred at ambient temperature for 2 hr and then cautiously treated successively with 1 ml of water, 1 ml of a 20% sodium hydroxide solution and 3 ml of water. The mixture was stirred for 0.5 hr, filtered and the filtrate concentrated to give a gummy solid as residue. The gum was converted to the oxalic acid salt. The salt was recrystallized from 2-propanol and then from absolute ethanol-ethyl ether to give 3.5 g (39% yield) of the title compound as a white solid, mp 81°-87° C. (dec).

Analysis: Calculated for $C_{32}H_{37}F_2NO_8 \cdot 1.5H_2O$: C, 61.14; H, 6.41; N, 2.23. Found: C, 61.13; H, 5.97; N, 2.17.

EXAMPLE 19

4[[3-[4-[Bis(4-fluorophenyl)hydroxymethyl]-1-piperidinyl]propyl]amino]benzeneacetic acid ethyl ester A solution of 4.18 g (0.02 mole) of ethyl p-nitrophenylacetate in 200 mL of ethanol is subjected to catalytic hydrogenation. The mixture is filtered to remove the catalyst and the filtrate is concentrated to obtain quantitative yield of ethyl 4-aminophenylacetate. To an agitated solution of the ethyl 4-aminophenylacetate and 2.02 g (0.02 mole) of triethylamine in 50 ml of dimethylformamide is added dropwise a solution of 7.58 g (0.020 mole) of 1-(3-chloropropyl)-α,α-bis(4-fluorophenyl)-4-piperidinemethanol in 20 ml of dimethylformamide. After stirring at ambient temperature for 4 hr the reaction mixture is heated at 70° C. for 4 hr. The reaction mixture is concentrated and the crude product partitioned between methylene chloride and water. The methylene chloride solution is washed with water, dried over anhydrous magnesium sulfate, and concentrated to yield the title compound.

EXAMPLE 20

4-[3-[4-[Bis(4-fluorophenyl)methyl]-3-piperidinyl]-propoxy]-3-methoxy-α-methylbenzenemethanol A solution of 4-[3-[4-[bis(4-fluorophenyl)methyl]-1-piperidinyl]propoxy]-3-methoxybenzeneethanone (4.4 g, 0.00885 mole) in 100 ml of 95% ethanol was added over a period of 15 minutes to a solution of sodium borohydride (3.0 g, 0.079 mole) in 250 ml of 95% ethanol. The resulting solution was stirred at room temperature for 2.5 hr. The mixture was concentrated, and the residual material partitioned between chloroform and a 5% sodium hydroxide solution. The organic layer was washed successively with a 5% sodium hydroxide solution and water, and the chloroform solution concentrated to an oil. Trituration with diethyl ether gave a white solid that was collected and recrystallized from methylene chloride-diethyl ether to obtain 2.16 g (40% yield) of the title compound as a white solid, mp 132°-135° C.

Analysis: Calculated for $C_{30}H_{35}F_2NO_3$: C, 72.72; H, 7.12; N, 2.83. Found: C, 72.28; H, 7.21; N, 2.52.

EXAMPLE 21

4-[3-[4-Bis(4-fluorophenyl)methanol]-1-piperidinyl]-propoxy]-3-methoxybenzoic acid hydrate (1:0.5)

A solution of 4-[3-[4-[bis(4-fluorophenyl)methyl]-1-piperidinyl]propoxy]-3-methoxybenzoic acid methyl ester (18.58 g, 0.0365 mole) in 400 ml of ethanol was treated with a solution of potassium hydroxide (16.8 g) in 50 ml water and the mixture heated at reflux temperature for 6 hr. The ethanol was then removed on a rotary evaporator, and the remaining solution treated with 200 ml of 1N sulfuric acid solution. The mixture was then made neutral to pH paper by addition of 5% sodium hydroxide solution. The mixture was extracted several times with chloroform. The combined extracts were dried over sodium sulfate, and concentrated to obtain a white solid. The solid was triturated with ether, the mixture chilled, and the white solid collected and dried in vacuo at 80° C. for 18 hrs to give 11.38 g (62% yield) of white, crystalline product, mp 123°-126° C.

Analysis: Calculated for $C_{29}H_{31}F_2NO_4.0.5H_2O$: C, 69.03; H, 6.39; N, 2.78. Found: C, 69.18; H, 6.32; N, 2.78.

EXAMPLE 22

1-[3-(4-Acetyl-2-methoxyphenoxy)propyl]-α,α-bis(4-fluorophenyl)-4-piperidineacetamide fumarate hydrate [1:0.5:0.5]

A mixture of α,α-bis(4-fluorophenyl)-4-piperidineacetamide (6.94 g, 0.021 mole), 1-[4-(3-chloropropoxy)-3-methoxyphenyl]ethanone (5.09 g, 0.021 mole), and potassium carbonate (5.53 g, 0.04 mole) was heated overnight at reflux in 350 ml of 1-butanol containing potassium iodide (0.2 g). The mixture was concentrated to dryness. The residue obtained was partitioned between chloroform and water. The chloroform layer was dried (sodium sulfate) and filtered. The solvent was removed to give a yellowish-brown residue. This material was converted to the fumarate, and the salt was recrystallized from methanol-diethyl ether. A white solid was obtained and dried in vacuo overnight at 80° C. This method provided 8.47 g (66.8%) of white, crystalline product, mp 258°-260° C. (dec).

Analysis: Calc. for $C_{31}H_{34}F_2N_2O_4.0.5C_4H_4O_4.0.5H_2O$: C, 65.66; H, 6.18; N, 4.64. Found: C, 65.88; H, 6.13; N, 4.65.

EXAMPLE 23

1-[4-[3-[4-[Aminobis(4-fluorophenyl)methyl]-1-piperidinyl]-3-methoxyphenyl]ethanone fumarate hydrate [1:2:1]

A mixture of α,α,-bis(4-fluorophenyl)-4-piperidinemethanamine (7.34 g, 0.0243 mole), 1-[4-(3-chloropropoxy)-3-methoxyphenyl]ethanone (5.88 g, 0.0243 mole) and potassium carbonate (5.53 g, 0.04 mole) was heated overnight at reflux in 500 ml of 1-butanol containing potassium iodide (0.2 g). The reaction was stripped to dryness, and the residue obtained was partitioned between chloroform and dilute sodium hydroxide. The chloroform layer was dried (sodium sulfate) filtered, and solvent removed to give a dark reddish brown oil (12.94 g). This oil was converted to the fumarate salt in methanol-diethyl ether. Two batches of the fumarate salt were obtained after additional recrystallizations from methanol (Batch I=6.43 g; Batch II=4.82 g) and drying in vacuo overnight at 80° C. This 11.25 g of faint yellow solid (mp 124°-128° C.) represents a yield of 61.0%.

Analysis: Calculated for $C_{30}H_{34}N_2O_3.2C_4H_4O_4.H_2O$: C, 60.15; H, 5.84; N, 3.69. Found: C, 59.84; H, 5.56; N, 3.56.

EXAMPLE 24

α,α-Bis(4-fluorophenyl)-1-[3-[4-(1-hydroxyethyl)-2-methoxyphenoxy]propyl]-4-piperidineacetamide Using the procedure of Example 20, 1-[3-(4-acetyl-2-methoxyphenoxy)propyl]-α,α-bis(4-fluorophenyl)-4-piperidineacetamide is reduced with sodium borohydride to give the title compound.

EXAMPLE 25

4-[3-[4-[Amino-bis(4-fluorophenyl)methyl]-1-piperidinyl]propoxy]-3-methoxy-α-methylbenzenemethanol Using the procedure of Example 20, 1-[4-[3-[4-[aminobis(4-fluorophenyl)methyl]-1-piperidinyl]-propoxy]-3-methoxyphenyl]-1-ethanone is reduced with sodium borohydride to give the title compound.

Formula I

| Ex | p | Ar | R | (A)d | (Q)n | Ring Position | m | (Bz) | l | W | Y | X | Salt |
|---|---|---|---|---|---|---|---|---|---|---|---|---|---|
| 1 | 1 | 4-F—C₆H₄— | 4-F—C₆H₄— | OH | — | 4 | 3 | 0 | 0 | 2-OCH₃ | 4-C(O)C(O)OH | H | — |
| 2 | 1 | 4-F—C₆H₄— | 4-F—C₆H₄— | OH | — | 4 | 3 | 0 | 0 | 2-OCH₃ | 4-CH(OH)C(O)OH | H | oxalate-2-propanol (1:1.5:1) |
| 3 | 1 | 4-F—C₆H₄— | 4-F—C₆H₄— | OH | — | 4 | 3 | 0 | 0 | 2-OCH₃ | 4-CH₂CH₂OH | H | oxalate-hydrate 2-propanol (1:1.5:0.5:1) |
| 4 | 1 | 4-F—C₆H₄— | 4-F—C₆H₄— | OH | — | 4 | 3 | 0 | 0 | 2-OCH₃ | 4-CH₂OH | H | — |
| 5 | 1 | 4-F—C₆H₄— | 4-F—C₆H₄— | OH | — | 4 | 3 | 0 | 0 | 2-OCH₃ | 4-C(O)CH₂OH | H | — |
| 6 | 1 | 4-F—C₆H₄— | 4-F—C₆H₄— | OH | — | 4 | 3 | 0 | 0 | 2-OCH₃ | 4-CH(OH)CH₂OH | H | — |
| 7a | 1 | 3,4-F₂—C₆H₃— | 3,4-F₂—C₆H₃— | H | — | 4 | 3 | 0 | 0 | 2-OCH₃ | 4-C(O)C(O)OH | H | — |
| 7b | 1 | 2,4-F₂—C₆H₃— | 2,4-F₂—C₆H₃— | H | — | 4 | 3 | 0 | 0 | 2-OCH₃ | 4-C(O)C(O)OH | H | — |
| 7c | 1 | 3-F—C₆H₄— | 3-F—C₆H₄— | — | — | 4 | 3 | 0 | 0 | 2-OCH₃ | 4-C(O)C(O)OH | H | — |
| 7d | 1 | 4-F—C₆H₄— | 4-F—C₆H₄— | OH | — | 4 | 3 | 0 | 0 | 2-OCH₃ | 4-C(O)C(O)OH | H | — |
| 7e | 1 | 4-F—C₆H₄— | 4-F—C₆H₄— | —C≡N | — | 4 | 3 | 0 | 0 | 2-OCH₃ | 4-C(O)C(O)OH | H | — |
| 7f | 0 | 4-F—C₆H₄— | 4-F—C₆H₄— | —C≡N | — | 3 | 3 | 0 | 0 | 2-OCH₃ | 4-C(O)C(O)OH | H | — |
| 8a | 1 | 3,4-F₂—C₆H₃— | 3,4-F₂—C₆H₃— | H | — | 4 | 3 | 0 | 0 | 2-OCH₃ | 4-CH(OH)C(O)OH | H | — |
| 8b | 1 | 4-F—C₆H₄— | 4-F—C₆H₄— | H | — | 4 | 3 | 0 | 0 | 2-OCH₃ | 4-CH(OH)C(O)OH | H | — |
| 8c | 1 | 2,4-F₂—C₆H₃— | 2,4-F₂—C₆H₃— | — | — | 4 | 3 | 0 | 0 | 2-OCH₃ | 4-CH(OH)C(O)OH | H | — |
| 8d | 1 | 3-F—C₆H₄— | 3-F—C₆H₄— | OH | — | 4 | 3 | 0 | 0 | 2-OCH₃ | 4-CH(OH)C(O)OH | H | — |
| 8e | 1 | 4-F—C₆H₄— | 4-F—C₆H₄— | —C≡N | — | 4 | 3 | 0 | 0 | 2-OCH₃ | 4-CH(OH)C(O)OH | H | — |
| 8f | 0 | 4-F—C₆H₄— | 4-F—C₆H₄— | —C≡N | — | 3 | 3 | 0 | 0 | 2-OCH₃ | 4-CH(OH)C(O)OH | H | — |
| 9a | 1 | 3,4-F₂—C₆H₃— | 3,4-F₂—C₆H₃— | H | — | 4 | 3 | 0 | 0 | 2-OCH₃ | 4-CH₂CH₂OH | H | — |
| 9b | 1 | 4-F—C₆H₄— | 4-F—C₆H₄— | H | — | 4 | 3 | 0 | 0 | 2-OCH₃ | 4-CH₂CH₂OH | H | — |
| 9c | 1 | 2,4-F₂—C₆H₃— | 2,4-F₂—C₆H₃— | — | — | 4 | 3 | 0 | 0 | 2-OCH₃ | 4-CH₂CH₂OH | H | — |
| 9d | 1 | 3-F—C₆H₄— | 3-F—C₆H₄— | OH | — | 4 | 3 | 0 | 0 | 2-OCH₃ | 4-CH₂CH₂OH | H | — |
| 9e | 1 | 4-F—C₆H₄— | 4-F—C₆H₄— | —C≡N | — | 4 | 3 | 0 | 0 | 2-OCH₃ | 4-CH₂CH₂OH | H | — |
| 9f | 0 | 4-F—C₆H₄— | 4-F—C₆H₄— | —C≡N | — | 3 | 3 | 0 | 0 | 2-OCH₃ | 4-CH₂CH₂OH | H | — |
| 10a | 1 | 3,4-F₂—C₆H₃— | 3,4-F₂—C₆H₃— | H | — | 4 | 3 | 0 | 0 | 2-OCH₃ | 4-CH₂OH | H | — |
| 10b | 1 | 4-F—C₆H₄— | 4-F—C₆H₄— | H | — | 4 | 3 | 0 | 0 | 2-OCH₃ | 4-CH₂OH | H | — |
| 10c | 1 | 2,4-F₂—C₆H₃— | 2,4-F₂—C₆H₃— | — | — | 4 | 3 | 0 | 0 | 2-OCH₃ | 4-CH₂OH | H | — |
| 10d | 1 | 3-F—C₆H₄— | 3-F—C₆H₄— | OH | — | 4 | 3 | 0 | 0 | 2-OCH₃ | 4-CH₂OH | H | — |
| 10e | 1 | 4-F—C₆H₄— | 4-F—C₆H₄— | —C≡N | — | 4 | 3 | 0 | 0 | 2-OCH₃ | 4-CH₂OH | H | — |
| 10f | 0 | 4-F—C₆H₄— | 4-F—C₆H₄— | —C≡N | — | 3 | 3 | 0 | 0 | 2-OCH₃ | 4-CH₂OH | H | — |
| 11a | 1 | 3,4-F₂—C₆H₃— | 3,4-F₂—C₆H₃— | H | — | 4 | 3 | 0 | 0 | 2-OCH₃ | 4-C(O)CH₂OH | H | — |
| 11b | 1 | 4-F—C₆H₄— | 4-F—C₆H₄— | H | — | 4 | 3 | 0 | 0 | 2-OCH₃ | 4-C(O)CH₂OH | H | — |
| 11c | 1 | 2,4-F₂—C₆H₃— | 2,4-F₂—C₆H₃— | — | — | 4 | 3 | 0 | 0 | 2-OCH₃ | 4-C(O)CH₂OH | H | — |
| 11d | 1 | 3-F—C₆H₄— | 3-F—C₆H₄— | OH | — | 4 | 3 | 0 | 0 | 2-OCH₃ | 4-C(O)CH₂OH | H | — |
| 11e | 1 | 4-F—C₆H₄— | 4-F—C₆H₄— | —C≡N | — | 4 | 3 | 0 | 0 | 2-OCH₃ | 4-C(O)CH₂OH | H | — |
| 11f | 0 | 4-F—C₆H₄— | 4-F—C₆H₄— | —C≡N | — | 3 | 3 | 0 | 0 | 2-OCH₃ | 4-C(O)CH₂OH | H | — |
| 12a | 1 | 3,4-F₂—C₆H₃— | 3,4-F₂—C₆H₃— | H | — | 4 | 3 | 0 | 0 | 2-OCH₃ | 4-CH(OH)CH₂OH | H | — |
| 12b | 1 | 4-F—C₆H₄— | 4-F—C₆H₄— | H | — | 4 | 3 | 0 | 0 | 2-OCH₃ | 4-CH(OH)CH₂OH | H | — |
| 12c | 1 | 2,4-F₂—C₆H₃— | 2,4-F₂—C₆H₃— | — | — | 4 | 3 | 0 | 0 | 2-OCH₃ | 4-CH(OH)CH₂OH | H | — |
| 12d | 1 | 3-F—C₆H₄— | 3-F—C₆H₄— | OH | — | 4 | 3 | 0 | 0 | 2-OCH₃ | 4-CH(OH)CH₂OH | H | — |
| 12e | 1 | 4-F—C₆H₄— | 4-F—C₆H₄— | —C≡N | — | 4 | 3 | 0 | 0 | 2-OCH₃ | 4-CH(OH)CH₂OH | H | — |

-continued

Formula I

Ar—C(A)d—R with (Q)n cyclohexene, N—(CH₂)ₘ—(B)z—(CH₂)ₗ—phenyl(W,Y,X), (piperidine)p

| Ex | p | Ar | R | (A)d | (Q)n | Ring Position | m | (B)z | l | W | Y | X | Salt |
|---|---|---|---|---|---|---|---|---|---|---|---|---|---|
| 12f | 0 | 4-F—C₆H₄— | 4-F—C₆H₄— | —C≡N | — | 3 | 3 | O | 0 | 2-OCH₃ | 4-CH(OH)CH₂OH | H | — |
| 13a | 1 | C₆H₅— | C₆H₅— | — | — | 4 | 3 | O | 0 | 2-OCH₃ | 4-C(O)C(O)OH | H | — |
| 13b | 1 | 4-F—C₆H₄— | 4-F—C₆H₄— | — | — | 4 | 3 | O | 0 | 2-OCH₃ | 4-C(O)C(O)OH | H | — |
| 13c | 1 | 4-F—C₆H₄— | 4-F—C₆H₄— | H | — | 4 | 3 | O | 0 | 2-OCH₃ | 4-C(O)C(O)OH | H | — |
| 13d | 1 | C₆H₅— | C₆H₅— | OH | — | 4 | 3 | O | 0 | 2-OCH₃ | 4-C(O)C(O)OH | H | — |
| 13e | 1 | C₆H₅— | C₆H₅— | H | — | 4 | 3 | O | 0 | 2-OCH₃ | 4-C(O)C(O)OH | H | — |
| 13f | 1 | C₆H₅— | C₆H₅— | — | — | 4 | 3 | O | 0 | 2-OCH₃ | 4-C(O)C(O)OH | H | — |
| 13g | 1 | 4-F—C₆H₄— | 4-F—C₆H₄— | H | CHOH | 4 | 3 | O | 0 | 2-OCH₃ | 4-C(O)C(O)OH | H | — |
| 13h | 1 | 4-F—C₆H₄— | 4-F—C₆H₄— | H | CH₂ | 4 | 3 | O | 0 | 2-OCH₃ | 4-C(O)C(O)OH | H | — |
| 13i | 1 | 4-F—C₆H₄— | 4-F—C₆H₄— | — | CH | 4 | 3 | O | 0 | 2-OCH₃ | 4-C(O)C(O)OH | H | — |
| 14a | 1 | 4-F—C₆H₄— | 2-pyridinyl-cyclohexyl- | OH | — | 4 | 3 | O | 0 | 2-OCH₃ | 4-C(O)C(O)OH | H | — |
| 14b | 1 | 4-F—C₆H₄— | 4-F—C₆H₄— | H | — | 4 | 3 | O | 0 | 2-OCH₃ | 4-C(O)C(O)OH | H | — |
| 15a | 1 | 4-F—C₆H₄— | 4-F—C₆H₄— | H | — | 4 | 3 | O | 0 | 2-OCH₃ | 4-CHOHC(O)OH | H | — |
| 15b | 1 | 4-F—C₆H₄— | 4-F—C₆H₄— | OH | — | 4 | 3 | O | 0 | 2-OCH₃ | 4-CHOHC(O)OH | H | — |
| 16 | 1 | 4-F—C₆H₄— | 4-F—C₆H₄— | OH | — | 4 | 3 | O | 0 | 2-OCH₃ | 4-C(O)CH₂OC(O)CH₃ | H | — |
| 17 | 1 | 4-F—C₆H₄— | 4-F—C₆H₄— | OH | — | 4 | 3 | O | 0 | 2-OCH₃ | 4-CH₂C(O)OC₂H₅ | H | — |
| 18 | 1 | 4-F—C₆H₄— | 4-F—C₆H₄— | OH | — | 4 | 3 | O | 0 | 2-OCH₃ | 4-CHOHCH₃ | H | — |
| 19 | 1 | 4-F—C₆H₄— | 4-F—C₆H₄— | OH | — | 4 | 3 | N | 0 | 2-OCH₃ | 4-CH₂C(O)OC₂H₅ | H | — |
| 20 | 1 | 4-F—C₆H₄— | 4-F—C₆H₄— | H | — | 4 | 3 | O | 0 | H | 4-CH(OH)CH₃ | H | — |
| 21 | 1 | 4-F—C₆H₄— | 4-F—C₆H₄— | OH | — | 4 | 3 | O | 0 | 2-OCH₃ | 4-C(O)OH | H | — |
| 22 | 1 | 4-F—C₆H₄ | 4-F—C₆H₄ | C(O)NH₂ | — | 4 | 3 | O | 0 | 2-OCH₃ | 4-C(O)CH₃ | H | oxalate hydrate |
| 23 | 1 | 4-F—C₆H₄ | 4-F—C₆H₄ | NH₂ | — | 4 | 3 | O | 0 | 2-OCH₃ | 4-C(O)CH₃ | H | — |
| 24 | 1 | 4-F—C₆H₄ | 4-F—C₆H₄ | C(O)NH₂ | — | 4 | 3 | O | 0 | 2-OCH₃ | 4-CH(OH)CH₃ | H | hemihydrate |
| 25 | 1 | 4-F—C₆H₄ | 4-F—C₆H₄ | NH₂ | — | 4 | 3 | O | 0 | 2-OCH₃ | 4-CH(OH)CH₃ | H | — |

PHARMACOLOGY METHODS

Antiallergy Screening Method—Rats

The primary screening method for demonstrating antiallergy properties of the compounds of Formula I is a modification of the procedure of R. R. Martel and J. Klicius, INTERNATIONAL ARCHIVES ALLERGY APPL. IMMUNOLOGY, 54, pp 205–209 (1977) which measures the effect of oral administration of the compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. The volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml)±S.D. A significant decrease ($p<0.05$) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency. It is suggested that when the compounds of the present invention are tested in this Method that they, i.e., Compounds of Formula I, will demonstrate significant antiallergy properties.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Mo.), at least 20 days prior to aerosol challenge by receiving 0.5 ml of EA-Al(OH)$_3$ conjugate (33 µg EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I cpd.) dissolved or suspended in 0.5% Tween 80 in distilled water or the control article (0.5 Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspnea, reeling, collapse and death. Upon collapsing, the animals are removed from the chamber. Animals are considered protected if they do not collapse within 5 min of exposure to the aerosolized antigen. The number of animals that collapse in each group is recorded. ED$_{50}$ for collapse is calculated by the method of Litchfield and Wilcoxon (1949), J. PHARMACOL. EXP. THERAP. 95, 99–113 for evaluation of dose-effect experiments. Comparisons of ED$_{50}$s from different experimental trials and determinations of relative potency are determined by the Litchfield and Wilcoxon method, ibid. The following conditions must be met before an experiment is acceptable:

1) control group shows collapse in $\frac{7}{8}$ or 8/8 animals, and
2) Theophylline reference group shows protection in $\frac{3}{4}$ or 4/4 animals treated 1 hr or 5 hr prior to antigen exposure. It is expected that compounds of Formula I, when tested in this manner will again exhibit antiallergy properties.

Screening Method for Calcium Channel Blocking Activity in Isolated Rabbit Aorta A non-fasted rabbit is killed by cervical dislocation. Spiral arterial strips are prepared from the thoracic aorta by the method of Furchgott, R. F., and Bhadrakom, S. (1953), J. PHARMACOL. EXP. THER. 108:129–43. The strips suspended in water-jacketed, 10 ml, organ baths that are kept at 37° C. and aerated with a mixture of 95% oxygen and 5% carbon dioxide. An isometric recording of tissue response is made with a Grass force-displacement transducer (Model FT03C) and a Grass polygraph.

The loading tension on the strips is about 1 g. About 90 min is allowed for maximum relaxation to occur, and during this time the bath is changed at 15 to 20 min intervals. The bath contains a physiological solution, hereafter referred to as normal bath solution, prepared in glass-distilled water and adjusted to pH 7.4. The composition of the solution in millimoles per liter will be

| | |
|---|---|
| sodium chloride | 120.0 |
| potassium chloride | 5.6 |
| calcium chloride | 2.6 |
| magnesium chloride hexahydrate | 1.2 |
| sodium dihydrogen phosphate hydrate | 1.5 |
| sodium bicarbonate | 25.0 |
| glucose | 9.1 |

Strips are first checked for viability based on their response to norepinephrine at a final bath concentration of $10^{-5}M$; then they are washed with the normal bath solution until resting tension has returned to baseline. Following this, the normal bath solution is replaced with a physiological solution, hereafter referred to as a calcium-free bath solution, having the same pH and composition as the normal bath solution except that the calcium is omitted. Strips are then incubated in this calcium-free solution for 10 min. During this time the solution is exchanged by fresh physiological (calcium-free) solution three times.

Strips are then tested for completeness of calcium depletion by incubation for 15 min in potassium depolarizing solution. The composition of the depolarizing solution in millimoles per liter is

| | |
|---|---|
| sodium chloride | 32.2 |
| potassium chloride | 100.0 |
| magnesium chloride hexahydrate | 1.2 |
| trihydroxymethyl hydrochloride | 12.0 |
| glucose | 9.1 |

The solution is prepared in glass-distilled water and adjusted to pH 7.4. If the strips contract, they will be washed with physiological solution and then reincubated in the depolarizing solution. The process is repeated if necessary until the strips are unresponsive and thus calcium depleated. Alternatively, the strips may be rewashed with depolarizing solution until they are calcium depleted.

Cumulative concentration response curves (controls) are made with calcium chloride as the agonist by the method of Van Rossum, J. M. (1963), ARCH. INT. PHARMACODYN. 143:299-330. Final bath concentrations of calcium chloride will be 0.1 millimolar, 0.3 millmolar, and 1.0 millimolar (See Godfraind, T. & Kaba, A (1969) BRIT. J. PHARMACOL. 36:549-60). Responses are allowed to reach a plateau before adding the next increment of calcium chloride.

After control responses are obtained, the strips are washed with normal bath solution containing test drug (Formula I) at $10^{-7}$ molar concentration for about one hour at 15-20 min intervals (see Broekaert, A. and Godfraind, T. (1979) Europ. J. Pharmacol. 53:281-288). During this time the tissues have returned to resting tension.

The strips are then incubated in the physiological solution (calcium-free) for 10 min and finally in the depolarizing solution for 15 min, both of which solutions at this point contain Formula I test drug. If the strips contract in the depolarizing solution, they will be washed as mentioned above until unresponsive. The cumulative concentration response to calcium chloride is then made over the range of concentrations used for the control determination.

As a final test to determine selectivity and whether α-blocking activity is present, the strips are washed with the normal bath solution containing the research compound until the resting tension is again at baseline. The strips are then retested for their response to norepinephrine at a final bath concentration of $10^{-5}$ molar.

In the foregoing primary screen, a minimum of 2 strips are used to test each drug at $10^{-7}$ molar. Those compounds which consistently produce at least 20% inhibition of the calcium induced contractions will be tested further. For those test drugs giving interesting positive results, a $pA_2$ value may be obtained, see Van Rossum (1963) ibid. Reference articles which may be used for comparison are lidoflazine, diltiazem, verapamil, nifedipine or other appropriate drugs. It is expected that the compounds of Formula I when tested by this procedure will demonstrate calcium channel blocking activity.

Test Method for Antihypertensive Effect of Orally Administered Drugs to Unanesthetized Spontaneously Hypertensive Rats Surgical Preparation of Rats Charles River, spontaneously hypertensive rats are anesthetized with sodium pentobarbital (50 mg/kg, IP). The abdomen and the top of head are shaved and cleaned. A midline incision, approximately 5 mm long, is made in the skin of the dorsal surface of the animal's neck. Brass tubing, 22 cm long with a slight bend in the end, is passed through the incision, under the skin diagonally down the animal's back and around to the right side of the lower abdomen of the rat.

The animal is then taped to the table in a supine position. A midline incision approximately 4 cm long is made with scissors in the skin and another through the abdominal muscle wall. With small blunt hemostats, the skin is separated from the abdominal muscle at the midline to expose the tip of the brass tube. A small opening is made through the abdominal muscle at the appropriate angle with the blunt tips of the hemostats.

The distal end of a modified Week's cannula is inserted in the abdominal cavity and the other end is threaded through the brass tube until it exits at the base of the animal's neck. The brass tubing is removed and the 7 mm cured polyethylene tip of the cannula is aligned and positioned for insertion into the abdominal aorta. The positioned cannula is filled with isotonic saline.

The abdominal viscera is gently moved to the side, exposing the aorta in the region of bifurcation. The aorta is isolated and 2 silk ligatures, 1 to 1.5 cm apart, are placed around it. The ligatures are used to briefly and gently occlude blood flow. The abdominal aorta is punctured craniad to the bifurcation with the tip of a 23-gauge hypodermic needle. The needle is removed, and the tip of the cannula inserted through this opening toward the heart. Caution is taken to keep the tip vertically aligned in the aorta. Blood is allowed to flow back through the cannula to check correct insertion. The cannula is cleared of blood with a 0.4 cc flush of isotonic saline. The stability of the cannula in the artery is ensured by suturing the ligature tied around the cannula to the dorsal muscle layers directly beside the aorta. The cannula is also satured to the abdominal wall at the point of exit. The abdominal viscera is repositioned, and the abdominal wall and skin sutured in separate layers with blanket stitch. The animal is given 0.2 ml Combiotic ® (procaine penicillin G and dihydrostreptomycin sulfate).

The end of the cannula exteriorized at the base of the neck is tied off and passed through an L-shaped piece of aluminum tubing fastened to the skull by screws and dental cement (Purdy and Ashbrook, 1978, J. PHARM. PHARMACOLOGY 30:436-41).

For protection and attachment of the cannula to the cage, the cannula is inserted through a length of flexible metal spring, which is attached to the aluminum tubing and to a part of a swivel device that permits the animal to move with relative freedom around the cage. During recovery, each rat is given a bottle of 5% dextrose containing terramycin (1 tsp. Pfizer Terramycin soluble powder/L 5% dextrose) to drink.

Blood Pressure Recordings

On the day following surgery, the tied-off cannula is reopened and attached to the swivel device. One end of a saline filled length of polyethylene 50 tubing is attached to the swivel and the other to a Statham pressure transducer (Model P23ID) creating a continuous saline-arterial connection. Continuous tracings from the direct aortic blood pressure are recorded on a Grass polygraph (Model 7). Heart rate is determined from the blood pressure pulse.

The electrical output of the blood pressure signal from the polygraph is fed into a Buxco Channel Cardiovascular analyzer (Model 12). The blood pressure signals are averaged for a 1-min period and measurements of blood pressure and heart rate is printed on a Texas Instruments data terminal (Model 700 ASR).

Maintenance of Rats

To maintain patency of cannula and to permit the animal to be used for maximum time, animals are continuously infused with heparin in sterile saline (2 mg/ml) at a rate of 0.05 to 0.06 ml/hr. Purina Mouse Chow and water are available ad libitum. A solution containing 5% dextrose and terramycin is given once weekly. Surgically prepared rats may be used more than once during a study. A minimum of 3 days must lapse before rats are used again. A rat is used only once in a dosage group.

Experimental Procedure

Each surgically prepared rat is individually housed in a separate cage. Each cage is labeled with the lot number and sequential rat number. Single doses of 10, 20, and 30 mg/kg of the test drug calculated on free base content is administered orally by using a syringe and size 16 gavage tube. Control article is PEG-300:saline at ratio of 1:1. Reference articles are verapamil and nifedipine. The carrier for compounds of Formula I and verapamil is PEG-300:saline, 1:1, and for nifedipine, it is ethanol. The dosage volume for test and control articles is 1 ml/kg body weight. Arterial blood pressure and heart rate are measured in each rat prior to and at 30, 60, 90, 120, 180, 240, 300, 360 minutes and 24 hours after drug administration.

It is expected that the compounds of the present invention will display antihypertensive properties when tested in this testing procedure.

Procedure for Determinating Effect of Compounds on Coronary Blood Flow

The procedure used to determine the effect of the aforementioned compounds on coronary arterial blood flow is described as follows.

Mongrel dogs of either sex are anesthetized with phenobarbital sodium (100 mg/kg) and pentobarbital sodium (100 mg total dose). The trachea was surgically exposed, a tracheal tube is inserted and the dog is artifically respired with room air using a Harvard Model 613 Respirator. The heart was exposed by a left thoracotomy at the fourth intercostal space. An approximately 1.5 cm segment of the left anterior descending coronary artery is exposed and a Statham electromagnetic blood flow probe was implanted around the vessel. The flow probe cable is connected to a Statham Model 2201 Blood Flow Meter. Continuous recordings of carotid arterial blood pressure, and of coronary arterial blood flows, may be obtained using a Grass Model 5 Polygraph.

The compounds are administered via a femoral vein. Changes in both magnitude and duration of change in coronary blood flow from pre-drug levels are determined. Generally, multiple doses of the compounds to be tested are administered to a single dog. Appropriate intervals between doses are allowed to permit the blood flow to return to control levels.

It is expected that compounds of Formula I will be effective in increasing coronary blood flow in this test procedure.

Screening Procedure for Antihistamine Activity

The compounds of the present invention exhibit antihistaminic activity in guinea pigs. The method of testing is a modification of the procedure of Tozzi et al (Agents and Actions, Vol. 4/4, 264–270, 1974) as follows: Guinea pigs are fasted 18–24 hrs in individual cages. Water is available ad libitum. On the test day, animals in groups of 3 are injected intraperitoneally with 30 mg/kg of the test compound prepared in an appropriate vehicle. Thirty minutes later histamine at a dosage level of 1.2 mg/kg($=2\times$ the $LD_{99}$) is injected into a marginal ear vein. Survival of the guinea pigs for 24 hrs is positive evidence of antihistaminic activity. If the vehicle used for the test compound is other than water, its effect is established by testing an equal amount as a control. The dose protecting 50% of the animals ($PD_{50}$) from death may be established from dose-response curves.

Compounds of Formula I are expected to exhibit antihistaminic activity in this testing procedure.

Screening Procedure for Gastric Antisecretory Activity In Pyloric-Ligated Rats

Female Sprague-Dawley rats weighing 130–180 g are starved 24 hours in individual screen-bottom cages with water ad libitum. Animals are arranged into groups of 9 rats each for treated animals and 8 rats for controls. Each group is injected intraduodenally at the time of pyloric-ligation with test drug in doses of 25.0 mg/kg (0.2 ml/100 g body weight). Rats dosed with deionized water (2 ml/kg) served as controls. Four hours following ligation, rats are killed, the stomachs removed, gastric juice collected and the volume determined. Total hydrochloric acid output is determined by potentiometic titration to pH 7.0 endpoint using a Radiometer TTA-61 autopipetting titration system. Statistical analysis is performed by using the "Student's t-test" significance.

The compounds of Formula I are expected to demonstrate antisecrtory activity when tested in this test procedure.

Various modifications and equivalents will be apparent to one skilled in the art and may be made in the compounds and methods of the present invention without departing from the spirit or scope thereof, and it is therefore to be understood that the invention is to be limited by the scope of the appended claims.

Pharmaceutical Compositions and Administrations

Compositions for administration to living animals are comprised of at least one of the compounds of Formula I according to the methods of treatment of the invention in association with a pharmaceutical carrier or excipient. Effective quantities of the compounds may be administered in any one of various ways, for example, orally as in elixirs, capsules, tablets or coated tablets, parenterally in the form of sterile solutions, suspensions and in some cases intravenously in the form of sterile solutions, intranasally and to the throat or bronchial region in the form of drops, gargles, syrups, powders, etc. or subcutaneously. Suitable tableting excipients include lactose, potato and maize starches, talc, gelatin, stearic and silicic acids, magnesium stearate and polyvinyl pyrrolidone.

For the parenteral administration, the carrier or excipient can be comprised of a sterile parenterally acceptable liquid, e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the following guide to projected human oral dosages is derived by knowledge of the activity obtained in animal screening tests for the various indications in the methods of the invention compared to activity of known agents in the field in the same animal screening tests. However, the amount of the active compounds administered need not be limited by these comparisons due to uncertainty in transposing comparative animal data to human treatments.

Compositions useful for treating cardiac dysfunction are suitable for reducing blood pressure, controlling angina attacks and arrhythmias and are generally projected to be those within the following limits for hypertension and anti-angina dosage.

Oral dosages projected for hypertension for an adult human are of the order of 40-300 mg/day divided into 2 or 3 doses. Thus, for example, two capsules each containing 10-50 mg active agent of Formula I could be administered 2-3 times daily for blood pressure lowering.

Oral dosages projected for use in the treatment of angina for an adult human are of the order of 60-400 mg/day divided into 2 or 3 doses. Thus, for example, two capsules each containing 10-30 mg active agent of Formula I could be administered 2-5 daily to increase coronary blood flow.

Oral dosages projected for use an antihistamines for an adult human are of the order of 10-120 mg/day divided into 2 or 3 doses. Thus, for example, one or two capsules each containing 10-40 mg active agent of Formula I could be administered 2-3 times daily for temporary relief of cough due to minor throat and bronchial irritation which may occur with the common cold or with inhaled irritants.

Oral dosages projected for use as antisecretory agents for an adult human are of the order of 4 to 150 mg/day divided into 2 or 3 doses. Thus, for example, one or two doses each containing 0.5 to 50 mg active agent of Formula I could be administered 2-3 times daily for temporary relief due to excessive acid release in the stomach.

Generally the pharmacology tests on guinea pigs in comparison to certain other antiallergy drugs suggest an effective dose for an adult will be in the range of 0.5 to 10 mg for the more active compounds with a daily dosage amounting to about 2 to 40 mg/day. Based on the animal data, unit dosages containing an amount of compound equivalent to about 0.01 to 0.1 mg of active drug per kilogram of body weight are contemplated. Daily dosages of about 0.05 to 0.5 mg/kg of body weight are contemplated for humans and obviously several small dosages forms may be administered at one time. However, the amount of the active compounds administered need not be limited by these contemplations due to uncertainty in transposing animal date to human treatment.

Other routes of administration such as subcutaneous, intraperitoneal, intravenous, etc. are possible with dosage forms being adapted to the situation as will be obvious to one skilled in the art of medicine.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:

1. A method for treating type 1 allergic responses in a mammal, by administering an effective amount of a compound having the formula:

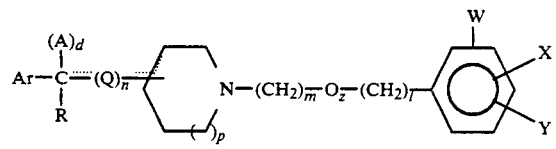

wherein,
Ar is

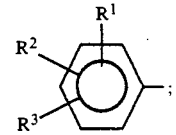

R is

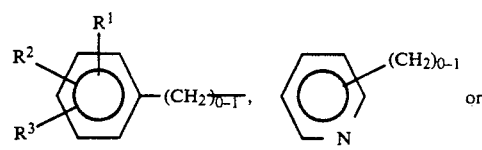

cycloalkyl-$(CH_2)_{0-1}$;

A is hydrogen, hydroxy, cyano, $C(O)NR^4R^5$ or $-NR^4R^5$,

Q is $-CH_2-$, $-CH-$ or $-CHOH-$;

d and n, same or different, are zero or one, and the dotted lines represent double bonds which may form consistent with the valence of carbon;

p is zero one or two;

m is zero to six inclusive;

l is zero or one;

W is hydrogen, loweralkyl, halo, nitro, loweralkoxy or hydroxy;

X is hydrogen, loweralkyl, halo, loweralkoxy or hydroxy;

Y is $-CH(OH)CH_2OH$, $-CH(OH)C(O)OH$, $-C(O)C(O)OH$, $-C(O)CH_2OH$, $-C(O)C(O)OCH_3$, $-C(O)C(O)OC_2H_5$, $-CH_2C(O)OC_2H_5$, $-CH(OH)C(O)OCH_3$, $-CH(OH)C(O)OC_2H_5$, or $-C(O)CH_2OC(O)CH_3$;

$R^1$, $R^2$ and $R^3$, same or different, are hydrogen, loweralkyl, halo, nitro, trifluoromethyl, cyano, loweralkoxy or hydroxy;

$R^4$ and $R^5$, same or different, are hydrogen, loweralkyl, phenyl, or phenylloweralkyl;

and the pharmaceutically acceptable salts thereof.

2. The method of claim 1 wherein the compound used is

4-[3-[4-[bis(4-fluorophenyl)hydroxymethyl]-1-piperidinyl]propoxy]-α-hydroxy-3-methoxybenzeneacetic acid or an addition salt thereof.

3. The method of claim 1 wherein the compound used is 2-(acetyloxy)-1-[4-[3-[bis(4-fluorophenyl)hydroxymethyl]-1-piperidinyl]propoxy]-3-methoxyphenyl]ethanone or an addition salt thereof.

4. The method of claim 1 wherein the compound used is

4-[3-[4-[bis(4-fluorophenyl)hydroxymethyl]-1-piperidinyl]propoxy]-3-methoxybenzeneacetic acid ethyl ester or an addition salt thereof.

5. A pharmaceutical composition comprised of a) an effective amount of a compound for treating type 1 allergic responses in a mammal selected from the group having the formula:

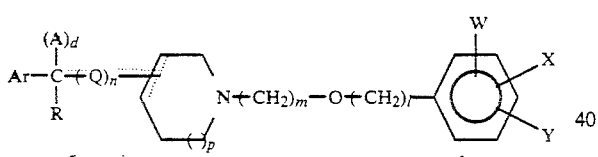

wherein,

Ar is

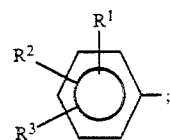

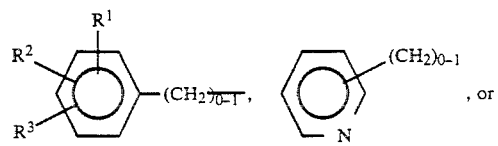

cycloalkyl-$(CH_2)_{0-1}$;

A is hydrogen, hydroxy, cyano, $C(O)NR^4R^5$ or $-NR^4R^5$,

Q is $-CH_2-$, $-CH-$ or $-CHOH-$;

d and n, same or different, are zero or one, and the dotted lines represent double bonds which may form consistent with the valence of carbon;

p is zero one or two;

m is zero to six inclusive;

l is zero or one;

W is hydrogen, loweralkyl, halo, nitro, loweralkoxy or hydroxy;

X is hydrogen, loweralkyl, halo, loweralkoxy or hydroxy;

Y is $-CH(OH)CH_2OH$, $-CH(OH)C(O)OH$, $-C(O)C(O)OH$, $-C(O)CH_2OH$ $-C(O)C(O)OCH_3$, $-C(O)C(O)OC_2H_5$, $-CH_2C(O)OC_2H_5$, $-CH(OH)C(O)OCH_3$, $-CH(OH)C(O)OC_2H_5$, or $-C(O)CH_2OC(O)CH_3$;

$R^1$, $R^2$ and $R^3$, same or different, are hydrogen, loweralkyl, halo, nitro, trifluoromethyl, cyano, loweralkoxy or hydroxy;

$R^4$ and $R^5$, same or different, are hydrogen, loweralkyl, phenyl, or phenylloweralkyl and the pharmaceutically acceptable salts thereof;

b) a pharmaceutical carrier thereof.

* * * * *